United States Patent
Begg et al.

(10) Patent No.: US 12,350,097 B2
(45) Date of Patent: Jul. 8, 2025

(54) DEVICES, SYSTEMS, AND METHODS FOR TRANS-VAGINAL, ULTRASOUND-GUIDED HYSTEROSCOPIC SURGICAL PROCEDURES

(71) Applicant: Covidien LP, Mansfield, MA (US)

(72) Inventors: Nikolai D. Begg, Wellesley, MA (US); Chad A. Pickering, Woburn, MA (US); Lisa M. Quealy, Dracut, MA (US); Jordan A. Whisler, Brookline, MA (US); Dalia P. Leibowitz, Cambridge, MA (US); Timothy J. Wood, Woburn, MA (US); Alyssa P. Brown, Pittsburgh, PA (US); Bradley T. Marcinek, Westford, MA (US); Scott J. Prior, Branford, CT (US)

(73) Assignee: Covidien LP, Mansfield, MA (US)

( * ) Notice: Subject to any disclaimer, the term of this patent is extended or adjusted under 35 U.S.C. 154(b) by 201 days.

(21) Appl. No.: 17/116,918

(22) Filed: Dec. 9, 2020

(65) Prior Publication Data
US 2021/0204910 A1    Jul. 8, 2021

Related U.S. Application Data

(60) Provisional application No. 62/958,045, filed on Jan. 7, 2020.

(51) Int. Cl.
*A61B 8/00* (2006.01)
*A61B 1/303* (2006.01)
(Continued)

(52) U.S. Cl.
CPC ............ *A61B 8/4209* (2013.01); *A61B 1/303* (2013.01); *A61B 8/12* (2013.01); *A61B 8/4444* (2013.01);
(Continued)

(58) Field of Classification Search
CPC ....... A61B 1/303; A61B 1/00071; A61B 1/05; A61B 1/0014; A61B 8/4209; A61B 8/12;
(Continued)

(56) References Cited

U.S. PATENT DOCUMENTS

| 5,166,787 A | 11/1992 | Irion |
| 5,351,678 A | 10/1994 | Clayton |

(Continued)

FOREIGN PATENT DOCUMENTS

| CN | 109069123 A | 12/2018 |
| JP | 61-122850 | 6/1986 |

(Continued)

OTHER PUBLICATIONS

International Search Report on Patentability and Written Opinion issued in corresponding International Application No. PCT/US2020/064108 dated Jul. 12, 2022, 11 pages.

(Continued)

*Primary Examiner* — Pascal M Bui Pho
*Assistant Examiner* — Neshat Baset
(74) *Attorney, Agent, or Firm* — Carter, DeLuca & Farrell LLP

(57) ABSTRACT

An ultrasound device includes a frame and an ultrasound sensor assembly. The frame includes first and second rails spaced-apart relative to one another and a longitudinal section defining a longitudinal axis. The longitudinal section has a distal end portion. The ultrasound sensor assembly configured to enable ultrasound imaging of a field of view and is attached to the distal end portion of the longitudinal section of the frame and oriented such that the field of view is disposed at an oblique angle relative to the longitudinal axis. A surgical system including the ultrasound device and a surgical instrument insertable therethrough is also provided.

10 Claims, 19 Drawing Sheets

(51) Int. Cl.
*A61B 8/12* (2006.01)
*A61B 17/12* (2006.01)
*A61B 17/32* (2006.01)
*A61M 25/10* (2013.01)

(52) U.S. Cl.
CPC ......... *A61B 8/483* (2013.01); *A61B 17/12136* (2013.01); *A61B 17/32002* (2013.01); *A61M 25/1002* (2013.01); *A61M 25/10181* (2013.11)

(58) Field of Classification Search
CPC ..... A61B 8/4444; A61B 8/483; A61B 8/4455; A61B 8/5207; A61B 8/54; A61B 8/085; A61B 8/4218; A61B 8/4245; A61B 8/4422; A61B 8/0841; A61B 17/12136; A61B 17/32002; A61B 17/4241; A61B 2090/3784; A61M 25/1002; A61M 25/10181
See application file for complete search history.

(56) References Cited

U.S. PATENT DOCUMENTS

| | | | |
|---|---|---|---|
| 5,935,057 | A | 8/1999 | Lichtman et al. |
| 6,174,307 | B1 | 1/2001 | Daniel et al. |
| 6,210,330 | B1* | 4/2001 | Tepper ............... A61B 17/4241 600/463 |
| 6,884,219 | B1 | 4/2005 | Pruter |
| 6,896,657 | B2 | 5/2005 | Willis |
| 6,936,048 | B2 | 8/2005 | Hurst |
| 6,960,166 | B1* | 11/2005 | Wong ..................... A61B 8/12 600/463 |
| 7,517,346 | B2 | 4/2009 | Sloan et al. |
| 7,520,856 | B2* | 4/2009 | Vaezy ................... A61B 8/462 601/3 |
| 7,591,785 | B2 | 9/2009 | Wendlandt et al. |
| 7,621,869 | B2 | 11/2009 | Ratnakar |
| 7,815,571 | B2 | 10/2010 | Deckman et al. |
| 7,874,986 | B2 | 1/2011 | Deckman et al. |
| 7,918,795 | B2 | 4/2011 | Grossman |
| 8,088,072 | B2 | 1/2012 | Munrow et al. |
| 8,206,300 | B2 | 6/2012 | Deckman et al. |
| 8,262,574 | B2 | 9/2012 | Placek et al. |
| 8,262,577 | B2 | 9/2012 | Munrow et al. |
| 8,298,145 | B2 | 10/2012 | Deckman et al. |
| 8,506,485 | B2 | 8/2013 | Deckman et al. |
| 8,992,427 | B2 | 3/2015 | Munrow et al. |
| 9,357,977 | B2 | 6/2016 | Grossman |
| 9,517,047 | B2 | 12/2016 | Grossman |
| 9,808,310 | B2 | 11/2017 | Grossman |
| 9,861,336 | B2 | 1/2018 | Munrow et al. |
| 9,987,080 | B2 | 6/2018 | Grossman |
| 10,058,342 | B2 | 8/2018 | Deckman et al. |
| 10,182,862 | B2 | 1/2019 | Grossman |
| 10,321,951 | B2 | 6/2019 | Placek et al. |
| 10,595,819 | B2 | 3/2020 | Deckman et al. |
| 10,610,197 | B2 | 4/2020 | Deckman et al. |
| 10,750,939 | B2 | 8/2020 | Begg |
| 2004/0092979 | A1* | 5/2004 | Burbank ............... A61B 17/122 606/158 |
| 2004/0181152 | A1 | 9/2004 | Zhang et al. |
| 2005/0203399 | A1 | 9/2005 | Vaezy et al. |
| 2005/0234294 | A1 | 10/2005 | Saadat et al. |
| 2005/0272975 | A1 | 12/2005 | McWeeney et al. |
| 2007/0112272 | A1 | 5/2007 | Park et al. |
| 2007/0213749 | A1 | 9/2007 | Kogasaka |
| 2009/0171218 | A1* | 7/2009 | Nygaard ................ A61B 8/445 600/564 |
| 2009/0259097 | A1 | 10/2009 | Thompson |
| 2009/0318758 | A1 | 12/2009 | Farr et al. |
| 2011/0160535 | A1 | 6/2011 | Bayer et al. |
| 2012/0116248 | A1 | 5/2012 | McWeeney et al. |
| 2012/0245416 | A1 | 9/2012 | Viola |
| 2013/0046137 | A1 | 2/2013 | Zhao et al. |
| 2014/0180001 | A1 | 6/2014 | von Grunberg et al. |
| 2014/0228875 | A1 | 8/2014 | Saadat |
| 2014/0276081 | A1* | 9/2014 | Tegels .................. A61B 8/4209 600/461 |
| 2017/0245838 | A1 | 8/2017 | Munrow et al. |
| 2017/0245891 | A1 | 8/2017 | Munrow et al. |
| 2017/0290626 | A1 | 10/2017 | Deckman et al. |
| 2017/0290627 | A1 | 10/2017 | Deckman et al. |
| 2017/0319174 | A1* | 11/2017 | Hill ...................... A61B 8/4245 |
| 2017/0340308 | A1 | 11/2017 | Cermak et al. |
| 2018/0008237 | A1 | 1/2018 | Venkataraman et al. |
| 2018/0042572 | A1 | 2/2018 | Munrow et al. |
| 2018/0078303 | A1 | 3/2018 | Grossman |
| 2018/0132927 | A1 | 5/2018 | Chen et al. |
| 2018/0318026 | A1 | 11/2018 | Placek |
| 2019/0008369 | A1 | 1/2019 | Hashiguchi et al. |
| 2019/0142370 | A1* | 5/2019 | Roy ..................... A61B 8/4416 600/431 |
| 2019/0192217 | A1 | 6/2019 | Grossman |
| 2019/0262080 | A1 | 8/2019 | Hammudi et al. |
| 2019/0269456 | A1 | 9/2019 | Placek et al. |
| 2019/0350648 | A1 | 11/2019 | Owens et al. |
| 2020/0229892 | A1 | 7/2020 | Munrow et al. |
| 2020/0275975 | A1* | 9/2020 | Chen .................. A61B 18/1492 |

FOREIGN PATENT DOCUMENTS

| | | |
|---|---|---|
| JP | S63150059 A | 6/1988 |
| JP | 2005-334187 | 12/2005 |
| WO | 2017158963 A1 | 9/2017 |

OTHER PUBLICATIONS

Invitation to Pay Additional Fees and Partial International Search Report issued in International Application No. PCT/US2020/064108 mailed Mar. 12, 2021, 12 pages.
International Search Report and Written Opinion issued in corresponding International Application No. PCT/US2020/064108 dated May 3, 2021, 18 pages.
Extended European Search Report 23192481.2 dated Dec. 22, 2023 8pp.
Japanese Office Action issued in corresponding Japanese Application No. 2022-541215 dated Oct. 8, 2024, 7 pages.
First Chinese Office Action issued in corresponding Chinese Application No. 202080092183.8 dated Nov. 30, 2024.
Japanese Office Action issued in corresponding Japanese Application No. 2022-541215 dated Apr. 15, 2025.

* cited by examiner

DEVICES, SYSTEMS, AND METHODS FOR TRANS-VAGINAL, ULTRASOUND-GUIDED HYSTEROSCOPIC SURGICAL PROCEDURES

CROSS-REFERENCE TO RELATED APPLICATIONS

This application claims the benefit of, and priority to, U.S. Provisional Patent Application No. 62/958,045, filed on Jan. 7, 2020, the entire contents of which are hereby incorporated herein by reference.

FIELD

The present disclosure relates to hysteroscopy and, more particularly, to devices, systems, and methods for trans-vaginal ultrasound-guided hysteroscopic surgical procedures.

BACKGROUND

Trans-vaginal hysteroscopy includes both intrauterine procedures, e.g., procedures performed within the uterine cavity, and intramural procedures, e.g., procedures performed within the uterine wall. Intrauterine procedures may require different approaches and/or instruments as compared to intramural procedures, and vice versa. Even within the same category, hysteroscopy procedures may require different approaches and/or instruments depending upon, for example, the procedure to be performed, patient anatomy, technique utilized, and/or other considerations.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with aspects of the present disclosure is a hysteroscopic system including an ultrasound device and a hysteroscope. The ultrasound device includes a proximal body, a shaft extending distally from the proximal body, and an ultrasound sensor assembly configured to enable ultrasound imaging. The ultrasound sensor assembly is disposed at the distal end portion of the shaft and oriented towards a distally-facing surface of the distal end portion of the shaft. The hysteroscope is configured for removable insertion at least partially through a lumen defined by the ultrasound device. The hysteroscope includes optics configured to enable visualization from a distal end portion of the hysteroscope.

In an aspect of the present disclosure, the system further includes a working instrument configured for removable insertion at least partially through a working channel defined through the hysteroscope. The working instrument may be a tissue resection device.

In another aspect of the present disclosure, at least the shaft defines the lumen extending longitudinally therethrough to an open distal end of the lumen at the distal end portion of the shaft.

In still another aspect of the present disclosure, the distal end portion of the shaft includes a distal foot extending distally beyond the open distal end of the lumen. The distal foot defines the distally-facing surface.

In yet another aspect of the present disclosure, the distally-facing surface at least partially surrounds the open distal end of the lumen.

In still yet another aspect of the present disclosure, the distally-facing surface is at least one of convex, conical, or curved.

In another aspect of the present disclosure, the ultrasound device further includes a movable sheath movable relative to the shaft. The movable sheath, in such aspects, defines the lumen therethrough.

In another aspect of the present disclosure, the movable sheath is coupled to the shaft via a pin-slot mechanism configured to enable pivoting and sliding of the movable sheath relative to the shaft.

A hysteroscopic ultrasound device provided in accordance with the present disclosure includes a proximal body, a shaft extending distally from the proximal body, and an ultrasound sensor assembly. At least the shaft defines a lumen extending longitudinally therethrough to an open distal end at a distal end portion of the shaft. The ultrasound sensor assembly is disposed at the distal end portion of the shaft and oriented towards a distally-facing surface of the distal end portion of the shaft. The ultrasound sensor assembly is configured to enable ultrasound imaging.

In an aspect of the present disclosure, the shaft and the proximal body cooperate to define the lumen.

In another aspect of the present disclosure, the distal end portion of the shaft includes a distal foot extending distally beyond the open distal end of the lumen. The distal foot, in such aspects, defines the distally-facing surface.

In yet another aspect of the present disclosure, the distally-facing surface at least partially surrounds the open distal end of the lumen.

In still another aspect of the present disclosure, the distally-facing surface is at least one of convex, conical, or curved.

In another aspect of the present disclosure, at least a portion of the distally-facing surface is angled relative to a longitudinal axis defined through the lumen.

In still yet another aspect of the present disclosure, a distal face of the distal end portion of the shaft is asymmetric.

Another hysteroscopic ultrasound device provided in accordance with the present disclosure includes a proximal body, a shaft extending distally from the proximal body to a distal end portion of the shaft, an ultrasound sensor assembly, and a movable sheath. The ultrasound sensor assembly is disposed at the distal end portion of the shaft and oriented towards a distally-facing surface of the distal end portion of the shaft. The ultrasound sensor assembly is configured to enable ultrasound imaging. The movable sheath is coupled to the shaft such that the movable sheath is at least pivotable with respect to the shaft. The movable sheath defines a lumen therethrough configured to at least partially receive a surgical instrument. In an angled position of the movable sheath relative to the shaft, a longitudinal axis of the movable sheath is disposed at an angle relative to a longitudinal axis of the shaft.

In an aspect of the present disclosure, the movable sheath is configured to pivot and translate relative to the shaft.

In another aspect of the present disclosure, the movable sheath is coupled to the shaft via a pin and slot mechanism.

In yet another aspect of the present disclosure, the movable sheath is movable from an in-line position, wherein the longitudinal axis of the movable sheath is disposed in substantially coaxial orientation relative to the longitudinal axis of the shaft, to the angled position.

An ultrasound device provided in accordance with the present disclosure includes a frame and an ultrasound sensor assembly. The frame includes first and second rails spaced-apart relative to one another and defines a longitudinal section defining a longitudinal axis and having a distal end portion. The ultrasound sensor assembly is configured to enable ultrasound imaging of a field of view, is attached to the distal end portion of the longitudinal section of the frame, and is oriented such that the field of view is disposed at an oblique angle relative to the longitudinal axis.

In an aspect of the present disclosure, the frame further includes an upright section disposed at an angle relative to the longitudinal section and a bend that interconnects the upright section and a proximal end portion of the longitudinal section.

In another aspect of the present disclosure, the ultrasound device further includes at least one spacer disposed between the first and second rails, configured to secure the first and second rails to one another and to maintain the spacing therebetween.

In yet another aspect of the present disclosure, the at least one spacer includes a distal spacer integrally formed with the ultrasound sensor assembly and disposed at the distal end portion of the longitudinal section of the frame.

In still another aspect of the present disclosure, the first and second rails are substantially parallel plates.

In still yet another aspect of the present disclosure, the ultrasound device further includes a sterile barrier disposed about the ultrasound sensor assembly and at least a portion of the longitudinal section of the frame.

In another aspect of the present disclosure, the ultrasound sensor assembly is detachable from the distal end portion of the longitudinal section of the frame. In such aspects, a sterile barrier disposable about the ultrasound sensor assembly is provided. The ultrasound sensor assembly, having the sterile barrier disposed thereabout, is attachable to the distal end portion of the longitudinal section of the frame.

In another aspect of the present disclosure, the ultrasound device further includes a locking mechanism disposed between the first and second rails and configured to selectively lock a surgical instrument, e.g., hysteroscope configured to receive a working instrument therethrough extending between the first and second rails in fixed position and orientation relative thereto.

In still yet another aspect of the present disclosure, the first and second rails are interconnected by a backspan along a portion of a length of the longitudinal section of the frame that is less than the length of the longitudinal section of the frame.

A surgical system provided in accordance with the present disclosure includes an ultrasound device according to any of the aspects above or otherwise herein, and a surgical instrument, e.g., a hysteroscope configured to receive a working instrument therethrough, configured for insertion between the first and second rails of the frame whereby the first and second rails constrain transverse movement of the surgical instrument In an aspect of the present disclosure, the surgical instrument is insertable between the first and second rails of the frame at the bend of the frame or the upright section of the frame in parallel or coaxial orientation relative to the longitudinal axis of the longitudinal section of the frame.

In another aspect of the present disclosure, the first and second rails constrain transverse movement of the surgical instrument while permitting axial translation, axial rotation, and vertical tilting of the surgical instrument when the surgical instrument is inserted between the first and second rails.

In still another aspect of the present disclosure, a sterile barrier is disposed about the ultrasound sensor assembly and at least a portion of the longitudinal section of the frame of the ultrasound device while the surgical instrument, when inserted between the first and second rails, remains external of the sterile barrier.

In yet another aspect of the present disclosure, the ultrasound device further includes a locking mechanism disposed between the first and second rails and configured to selectively lock the surgical instrument between the first and second rails in fixed position and orientation relative thereto.

Another surgical system provided in accordance with the present disclosure includes an ultrasound device and a surgical instrument. The ultrasound device includes a shaft having a body defining a longitudinal axis and including a lumen extending coaxially therethrough, and an ultrasound sensor assembly configured to enable ultrasound imaging of a field of view. The ultrasound sensor assembly is disposed at a distal end portion of the body of the shaft, offset relative to the longitudinal axis, and oriented such that the field of view is offset relative to the longitudinal axis. The surgical instrument is configured for removable insertion through the lumen of the body of the shaft and to extend distally from the distal end portion of the body of the shaft.

In an aspect of the present disclosure, the shaft further includes a foot extending distally from the body. In such aspects, the ultrasound sensor assembly may be disposed within the foot.

In another aspect of the present disclosure, the shaft further includes a leg extending distally from the body and a foot disposed at a distal end of the leg. In such aspects, the ultrasound sensor assembly may be disposed within the foot.

In still another aspect of the present disclosure, an annular volume is defined between an inner-most surface of the foot and an outer-most surface of the surgical instrument when the surgical instrument is inserted through the lumen and extends distally from the distal end portion of the body. In such aspects, the ultrasound device may be rotatable about the surgical instrument inserted therethrough while maintaining the annular volume regardless of a rotational orientation of the ultrasound device relative to the surgical instrument.

In yet another aspect of the present disclosure, the field of view is offset at an oblique angle relative to the longitudinal axis; in other aspects, at an acute angle relative to the longitudinal axis.

In another aspect of the present disclosure, the ultrasound sensor assembly is oriented towards a distal surface of the shaft that at least partially surrounds an open distal end of the lumen.

In still another aspect of the present disclosure, the ultrasound sensor assembly is oriented towards a distal surface of the shaft that includes at least one of convex, conical, or curved surface portion.

In another aspect of the present disclosure, the ultrasound sensor assembly is oriented towards a distal surface of the shaft and the distal surface is angled relative to the longitudinal axis.

A bias assembly may be provided in aspects. The bias assembly is configured to couple the ultrasound device with the surgical instrument and bias the ultrasound device distally about and relative to the surgical instrument.

The bias assembly, in aspects, may include a lock collar configured for fixed engagement about the surgical instrument, an outer sleeve configured to telescopically receive the shaft, and a biasing member disposed between the lock collar and the shaft to bias the shaft distally.

An inflatable balloon disposed about the body of the shaft may be provided, in aspects. In such aspects, the ultrasound device may further include a fluid outlet opening positioned distally of the inflatable balloon.

A method of surgery provided in accordance with aspects of the present disclosure includes inserting an ultrasound device transvaginally to position an ultrasound sensor assembly of the ultrasound device adjacent the cervix exteriority of the uterus, and inserting a surgical instrument through a lumen of the ultrasound device, through the cervix, and into the uterus.

In aspects, positioning the ultrasound sensor assembly adjacent the cervix exteriority of the uterus includes positioning the ultrasound sensor assembly in contact with a vaginal fornix.

In aspects, the method further includes generating an ultrasound image of at least a portion of the uterus using the ultrasound sensor assembly.

In aspects, the method further includes locking the surgical instrument in fixed position relative to the ultrasound device.

In aspects, the method further includes inserting a working instrument through the surgical instrument and into the uterus.

In aspects, the method further includes rotating the ultrasound device about the cervix.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
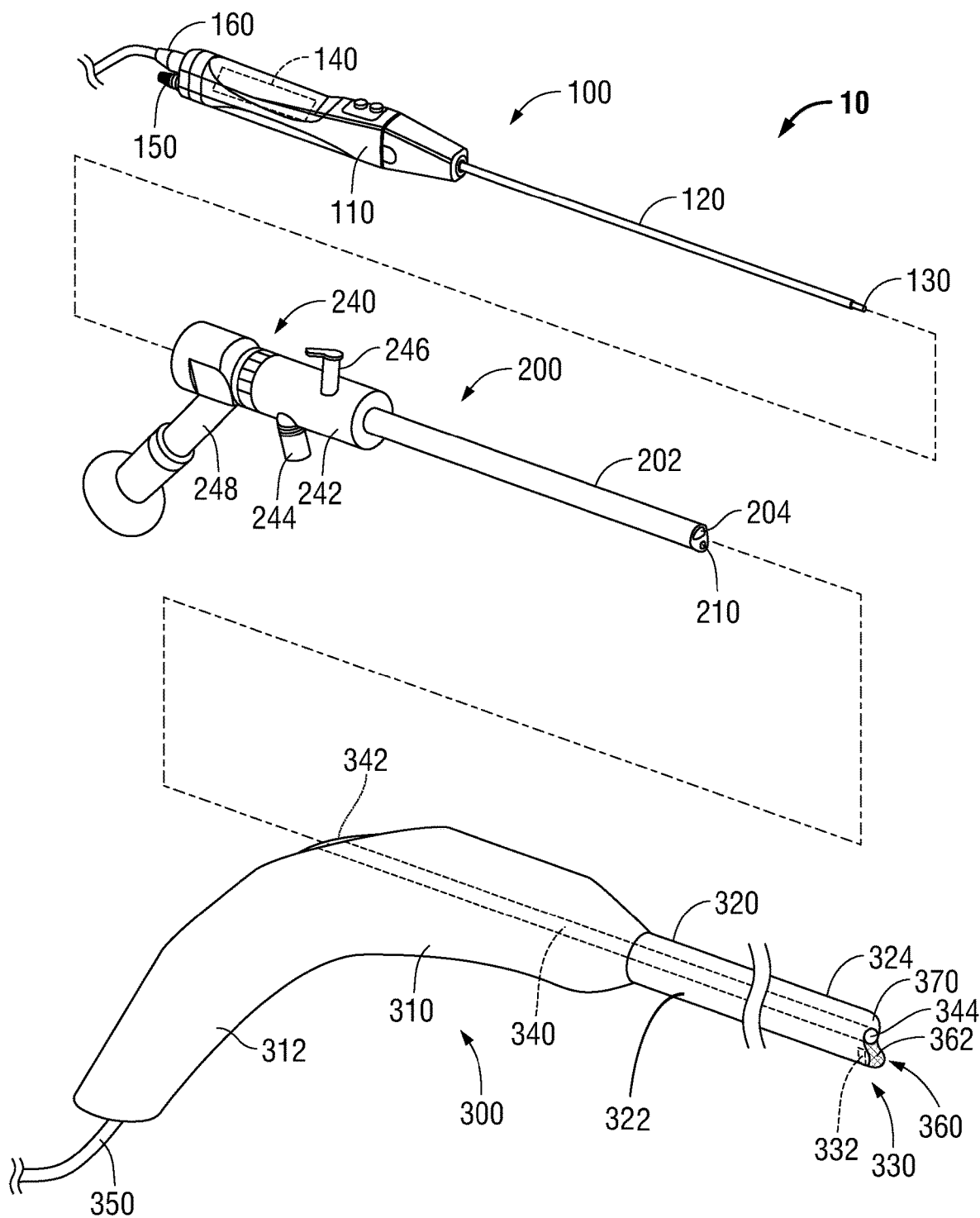
FIG. 1 is an exploded, perspective view of a hysteroscopic system in accordance with the present disclosure.

Referring to FIG. 1, a hysteroscopic system provided in accordance with the present disclosure is shown generally identified by reference numeral 10 including a working instrument 100, e.g., a tissue resection device, an ablation device, a biopsy device, etc.; a hysteroscope 200; and an ultrasound device 300. Ultrasound device 300 is configured for trans-vaginal insertion into position adjacent to or in abutment with the cervix. Hysteroscope 200 is configured for insertion through ultrasound device 300 and the cervix into the uterus. Working instrument 100 is configured for insertion through hysteroscope 200 and into the uterus to perform a surgical procedure in the uterine cavity and/or within the uterine wall.

Working instrument 100, as noted above, may be a tissue resection device, an ablation device, a biopsy device, or other suitable working instrument configured for use on or within the uterus. With respect to a tissue resection device, for example, working instrument 100 includes a housing 110, a shaft 120, a cutting member 130, a drive mechanism 140, an outflow port 150, and a cable 160. Housing 110 houses drive mechanism 140 therein and functions as a handle to enable a user to grasp working instrument 100. Drive mechanism 140 includes a motor and is operably coupled to cutting member 130 to drive rotation and/or translation of cutting member 130 relative to shaft 120. Drive mechanism 140 is adapted to connect to a control unit (not shown) via cable 160 for powering and controlling the motor, although working instrument 100 may alternatively be battery powered or manually powered. A suction source (not shown) incorporated into the control unit (not shown), or any other suitable vacuum-creating mechanism, may also be provided to facilitate withdrawal of fluid, tissue, and debris through working instrument 100 and outflow tube 150, as detailed below.

Shaft 120 of working instrument 100 extends distally from housing 110 and, in embodiments, is stationary relative to housing 110, although other configurations are also contemplated. Shaft 120 defines a window through a sidewall thereof towards a distal end thereof to provide access to cutting member 130 which is rotatably and/or translatably disposed within shaft 120 and, as noted above, operably coupled to drive mechanism 140. Cutting member 130 defines an opening providing access to the interior thereof and may include a serrated cutting edge surrounding the opening, although other suitable cutting edge configurations are also contemplated. Alternatively or additionally, shaft 120 may include a cutting edge defined about the window thereof.

In use of working instrument 100, upon activation, tissue is drawn through the window of shaft 120 and into the opening of cutting member 130. As tissue is drawn into the opening of cutting member 130, the tissue is resected via the rotation and/or translation of cutting member 130 relative to shaft 120, thus enabling the resected tissue to be drawn proximally through cutting member 130, along with fluid and debris. The resected tissue and fluid and debris are drawn proximally through cutting member 130 through outflow port 150 and outflow tubing (not shown) and, ultimately, to one or more collection canisters of a fluid management system (not shown).

Continuing with reference to FIG. 1, hysteroscope 200 includes an elongated tubular member 202 and a proximal body 240. Elongated tubular member 202 of hysteroscope 200 defines a working channel 204 configured to receive a working instrument therethrough, e.g., working instrument 100. Working channel 204 may also serve as a fluid inflow (or outflow) channel. Alternatively or additionally, a separate fluid inflow (or outflow) channel may be provided. Elongated tubular member 200 further includes optics 210 extending therethrough to enable visualization at the distal end of elongated tubular member 202.

Proximal body 240 of hysteroscope 200 includes a housing 242, a light post 244, a valve 246, and an arm 248. Light post 244 extends from housing 242 and is configured to connect to a light source, e.g., to illuminate a distal end of elongated tubular member 202 via one or more fiber optic strands (not shown) coupled to light post 244 and extending through elongated tubular member 202. Valve 246 is disposed in fluid communication with working channel 204 and is configured to enable the selective inflow and/or outflow of fluid to/from working channel 204. In configurations where multiple flow channels are provided, multiple valves may likewise be provided. Arm 248 is configured to connect to an imaging device, e.g., a camera, to capture images received via optics 210 and, thus, enable display of a video image of an internal surgical site as captured by optics 210.

Referring still to FIG. 1, ultrasound device 300 includes a proximal body 310, a shaft 320 extending distally from proximal body 310, and an ultrasound sensor assembly 330 disposed at a distal end portion 324 of shaft 320. Ultrasound device 300 further includes a longitudinal lumen 340 defined through proximal body 310 and shaft 320 and including an open proximal end 342 and an open distal end 344. Longitudinal lumen 340 may be coaxial with a longitudinal axis defined through shaft 320 or may be offset and/or angled relative thereto. Longitudinal lumen 340 is configured to permit passage of at least a portion of an endoscope device e.g., elongated tubular member 202 of hysteroscope 200, therethrough such that a distal portion of the elongated tubular member 202 extends through open distal end 344 of longitudinal lumen 340 and distally from shaft 320. Longitudinal lumen 340 may additionally or alternatively be configured to permit passage of other instrumentation, e.g., one or more working instruments, therethrough.

Figure 20:
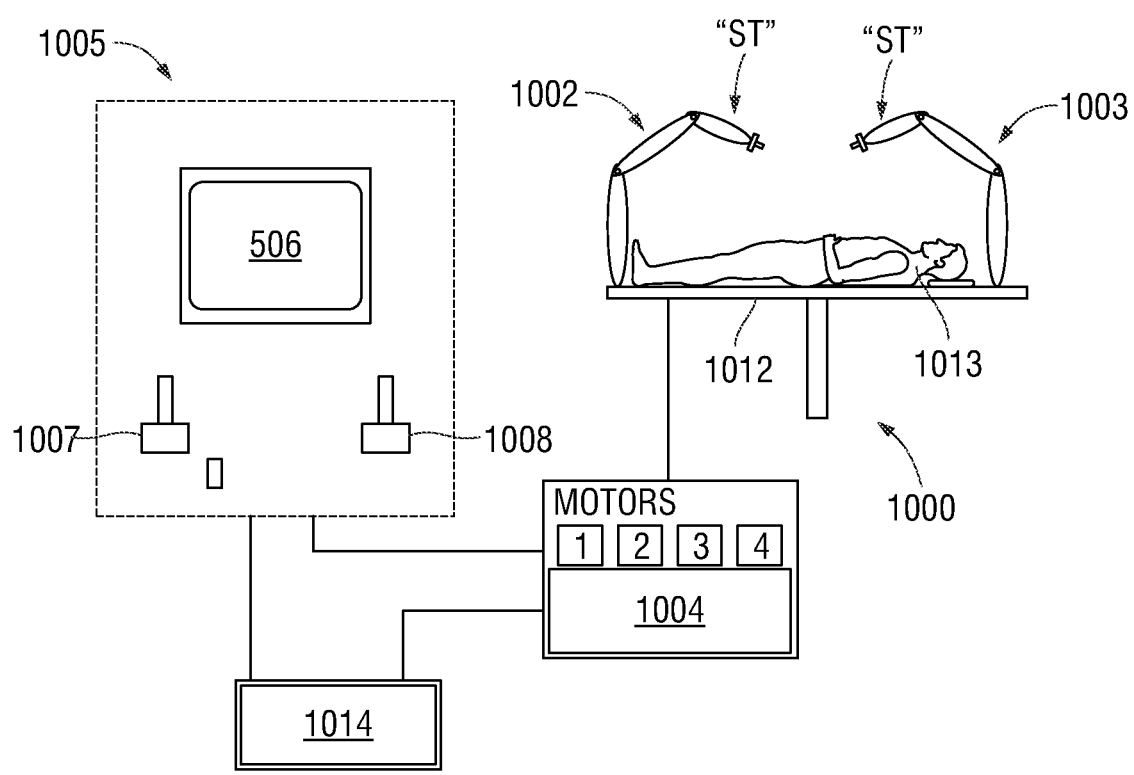
FIG. 20 is a schematic illustration of an exemplary robotic surgical system configured for use with the present disclosure.

Proximal body 310 of ultrasound device 300 may be configured as a handle including, for example, a pistol-style grip 312, although other handle configurations are also contemplated as are non-handle configurations, e.g., for mounting ultrasound device 300 and/or attaching ultrasound device 300 to a surgical robot arm (see FIG. 20). A cable 350 extends from proximal body 310 to connect ultrasound sensor assembly 330 of ultrasound device 300 to an ultrasound console (not shown), e.g., via wires (not shown) extending from ultrasound sensor assembly 330 through shaft 320, proximal body 310, and cable 350.

Shaft 320 of ultrasound device 300 is configured for trans-vaginal insertion into position adjacent or in abutment with the cervix such that distal end 344 of longitudinal lumen 340 is oriented towards the cervical canal to enable passage of hysteroscope 200 (or other suitable surgical instrumentation) through longitudinal lumen 340, out distal end 344 thereof, through the cervical canal and into the uterus. A body portion 322 of shaft 320 may define a cylindrical-shaped configuration and/or a distal end portion 324 of shaft 320 may be tapered, curved, and/or otherwise atraumatically configured to facilitate atraumatic insertion.

Ultrasound sensor assembly 330 includes one or more ultrasound sensors 332, e.g., ultrasound transducers, to enable ultrasound imaging of tissue, e.g., the uterus. Each ultrasound sensor 332 is configured to emit ultrasound waves, e.g., high-frequency sound waves, and to receive echoed waves produced by the reflection of the ultrasound waves against the various tissue structures encountered. The echoed waves received by each ultrasound sensor 332 are output to an image processing unit (not shown), e.g., by way of wires extending through shaft 320, proximal body 310, and cable 350. In embodiments, ultrasound sensor assembly 330 may be configured for 2D ultrasound imaging. In other embodiments, ultrasound sensor assembly 330 includes a plurality of ultrasound sensors 332 forming an ultrasound sensor array that defines a portion of a circle, a portion of a polygon, a partially-polygonal, partially-arcuate configuration, or other suitable configuration to enable reconstruction of a 3D ultrasound image therefrom for 3D ultrasound imaging. In this manner, when activated, ultrasound sensor assembly 330 enables ultrasound imaging of tissue, e.g., the cervix, uterus, and/or surrounding tissue.

Figure 2:
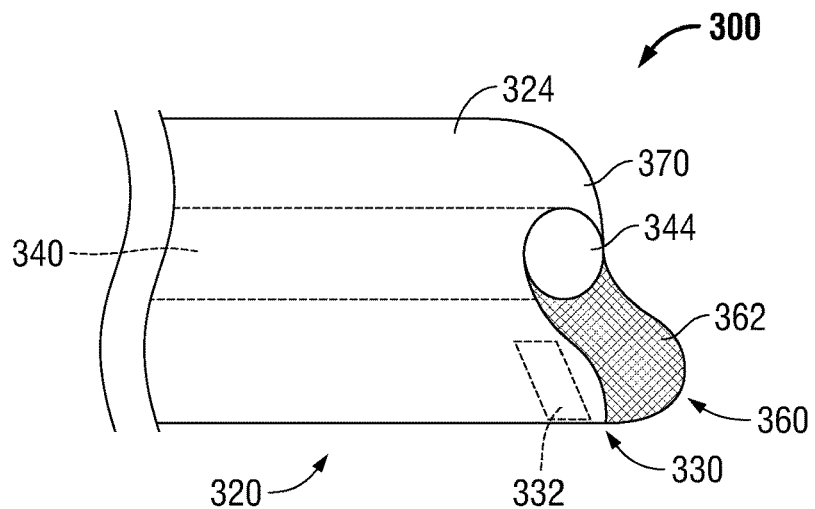
FIG. 2 is a perspective view of a distal end portion of the ultrasound device of the hysteroscopic system of FIG. 1.

Turning to FIG. 2, distal end portion 324 of shaft 320 defines a protruding foot 360 on one side of open distal end 344 of longitudinal lumen 340 that protrudes further distally as compared to a distal face portion 370 disposed on the other side of open distal end 344 of longitudinal lumen 340. Protruding foot 360 defines a curved distally-facing surface 362 including one or more curved sections. For example, distally-facing surface 362 of protruding foot 360 may include a concave surface portion extending distally and outwardly from distal end 344 of longitudinal lumen 340 followed by a convex surface portion extending distally and outwardly from the concave surface portion. Other suitable configurations are also contemplated. Regardless of the particular configuration, ultrasound sensor assembly 330 is positioned within protruding foot 360 with the sensor(s) 332 thereof oriented towards distally-facing surface 362 to emit ultrasound waves therefrom. Protruding foot 360 is configured for positioning adjacent or in abutment with the cervix such ultrasound sensor assembly 330 can be utilized for imaging e.g., the cervix, uterus, and surrounding tissue.

Figure 3:
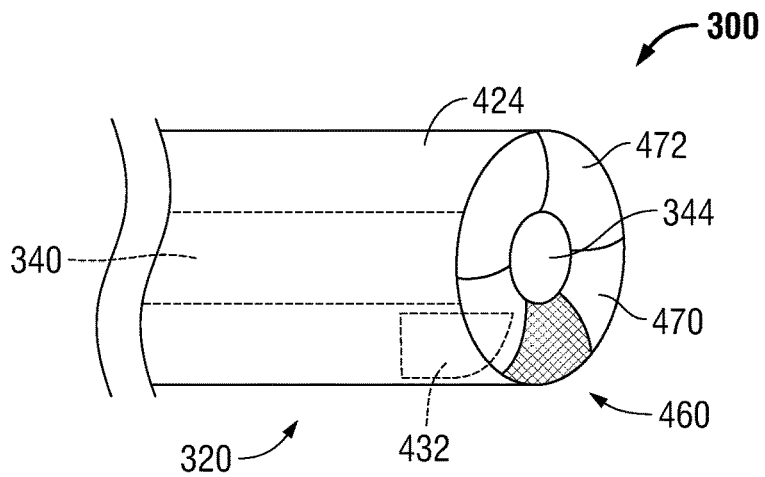
FIG. 3 is a perspective view of another configuration of the distal end portion of the ultrasound device of the hysteroscopic system of FIG. 1.

With reference to FIG. 3, in other configurations, distal end portion 424 of shaft 320 defines a distal face portion 470 surrounding open distal end 344 of longitudinal lumen 340. Distal face portion 470 is curved to define a radially-symmetric convex distally-facing surface 472 wherein an annular portion between open distal end 344 of longitudinal lumen 340 and the outer perimeter of distal end portion 424 of shaft 320 protrudes further distally as compared to the portions of surface 472 adjacent open distal end 344 of longitudinal lumen 340 and the outer perimeter of distal end portion 424 of shaft 320. Ultrasound sensor assembly 430 is positioned at distal end portion 424 of shaft 320 and may extend about a portion or the entirety of distal face portion 470. Sensors 432 of ultrasound sensor assembly 430 are oriented towards surface 472 to emit ultrasound waves therefrom such that ultrasound sensor assembly 430 can be utilized for imaging e.g., the cervix, uterus, and surrounding tissue.

Figure 4:
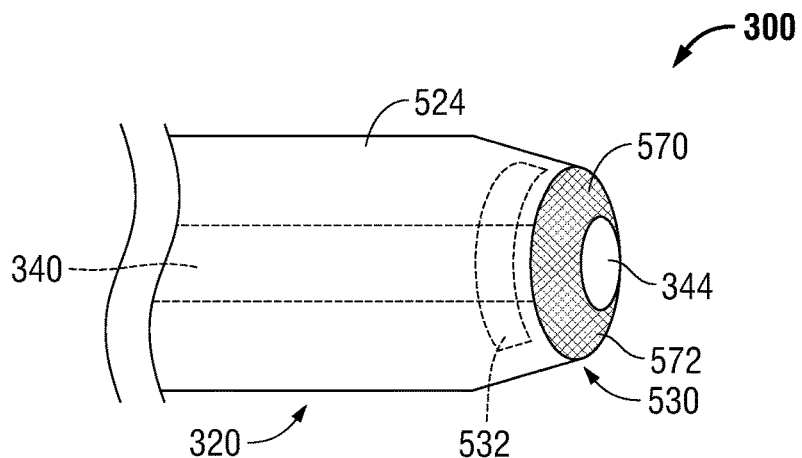
FIG. 4 is a perspective view of still another configuration of the distal end portion of the ultrasound device of the hysteroscopic system of FIG. 1.

Referring to FIG. 4, in other configurations, distal end portion 524 of shaft 320 defines a distal face portion 570 surrounding open distal end 344 of longitudinal lumen 340 that tapers radially inwardly in a proximal-to distal direction. Thus, distal face portion 570 defines a distally-facing surface 572 wherein the portion thereof adjacent open distal end 344 of longitudinal lumen 340 protrudes further distally as compared to the portion adjacent the outer perimeter of distal end portion 524 of shaft 320. Ultrasound sensor assembly 530 is positioned at distal end portion 524 of shaft 320 and may extend annularly about the entirety thereof (as shown), or just a portion thereof. Sensors 532 of ultrasound sensor assembly 530 are oriented towards surface 572 to emit ultrasound waves therefrom such that ultrasound sensor assembly 430 can be utilized for imaging e.g., the cervix, uterus, and surrounding tissue.

Figure 5:
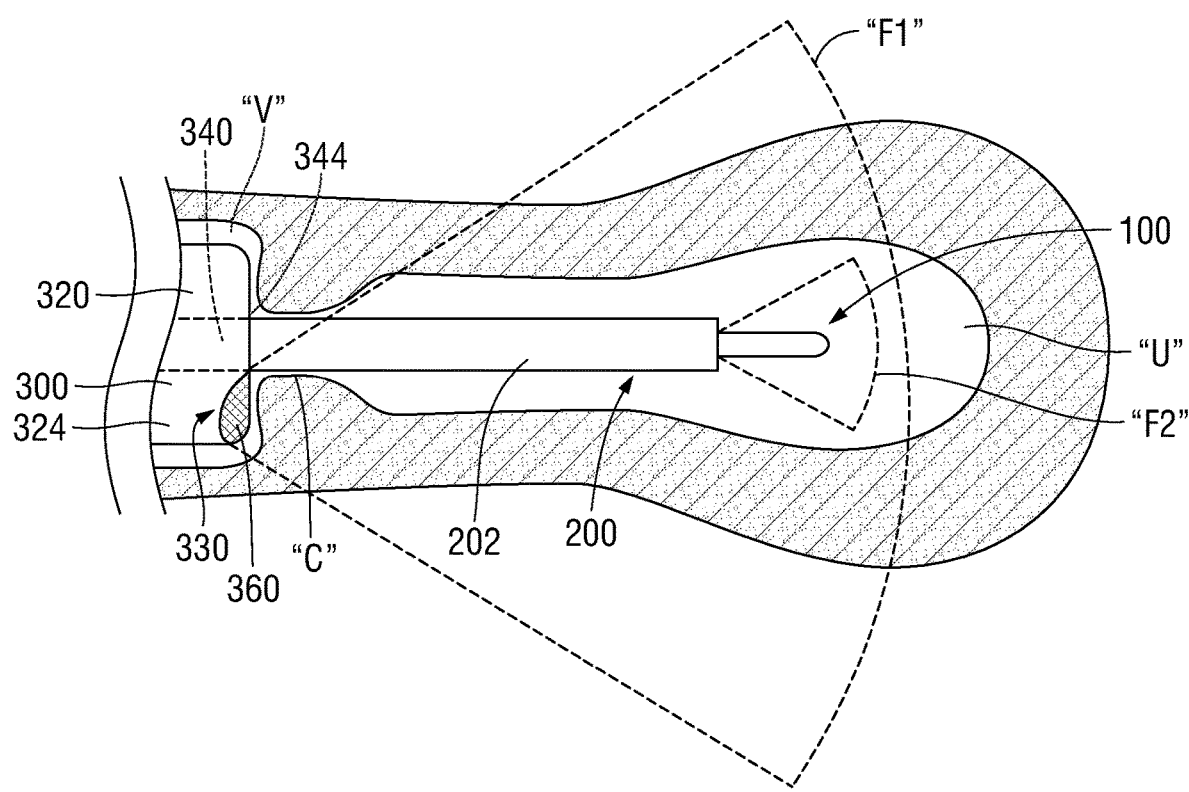
FIG. 5 is a side view of the hysteroscopic system of FIG. 1 positioned intra-vaginally for performing a procedure on or within a uterus.

Turning to FIG. 5, hysteroscopic system 10 is shown in use wherein ultrasound device 300 is inserted trans-vaginally through the vaginal canal "V" such that distal end portion 324 of shaft 320 thereof is disposed adjacent or in abutment with the cervix "C." In this position, more specifically, protruding foot 360, including ultrasound sensor assembly 330, is positioned adjacent or in abutment with the cervix "C" to enable ultrasound imaging of a field of view "F1" including the uterus "U" and surrounding tissue. Further, in this position, open distal end 344 of longitudinal lumen 340 is oriented with the cervical canal and elongated tubular member 202 extends therefrom, through the cervix "C" and into the uterus "U." In this manner, hysteroscope 200 may be utilized for visualization within the uterus "U," e.g., providing a field of view "F2," together with or separately from the ultrasound imaging. Hysteroscope 200 may also be used for the introduction of fluid into and/or the removal of fluid from the uterus "U" and/or for passage of a working instrument 100, e.g., a tissue resection device, ablation device, biopsy device, etc., therethrough and into the uterus "U" to perform one or more hysteroscopic tasks therein (e.g., within the uterus "U") or therethrough (e.g., within the uterine wall). The use of ultrasound imaging of the uterus "U" from the exterior thereof and/or visualization of the uterus "U" from within the uterine cavity provides increased visibility for performing various different hysteroscopic tasks without the need to swap out instruments supporting different imaging modalities and/or providing different imaging perspectives.

Figure 6:
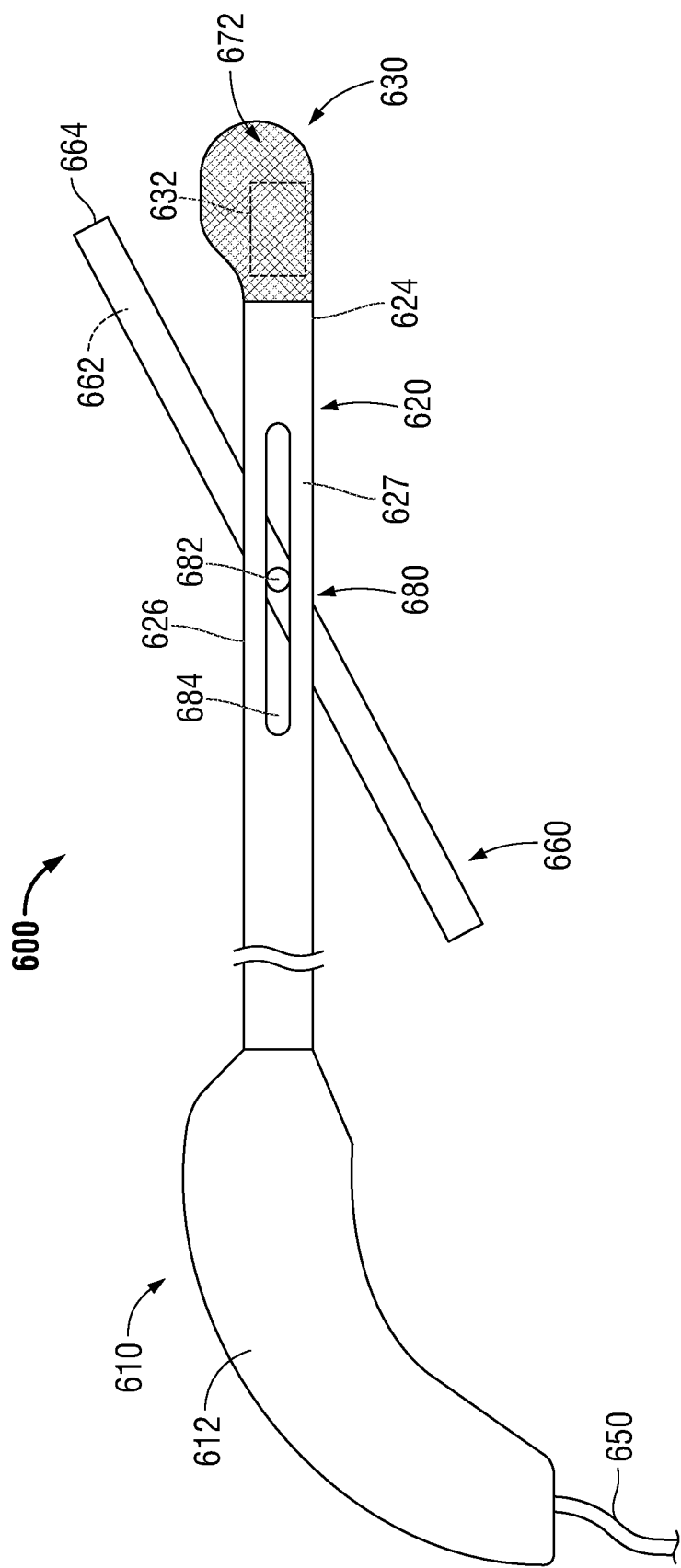
FIG. 6 is a side view of another ultrasound device configured for use with the hysteroscopy system of FIG. 1.
Figure 7:
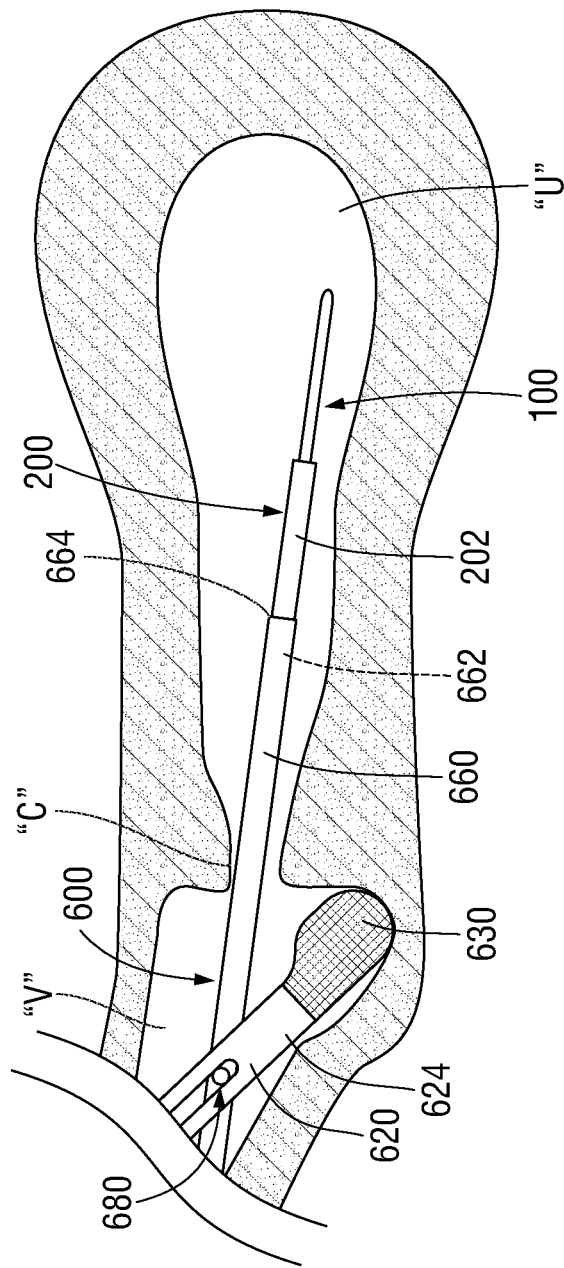
FIG. 7 is a side view of the ultrasound device of FIG. 6 positioned intra-vaginally for performing a procedure on or within a uterus utilizing a hysteroscope and a working instrument.

FIGS. 6 and 7 illustrate another ultrasound device 600 provided in accordance with the present disclosure. Ultrasound device 600 includes a proximal body 610, a shaft 620 extending distally from proximal body 610, an ultrasound sensor assembly 630 disposed at a distal end portion 624 of shaft 620, and a movable sheath 660.

Proximal body 610 of ultrasound device 600 may be configured as a handle including, for example, a pistol-style grip 612, although other handle configurations are also contemplated as are non-handle configurations, e.g., for mounting ultrasound device 600 and/or attaching ultrasound device 600 to a surgical robot arm (see FIG. 20). A cable 650 extends from proximal body 610 to connect ultrasound sensor assembly 630 of ultrasound device 600 to an ultrasound console (not shown), e.g., via wires (not shown) extending from ultrasound sensor assembly 630 through shaft 620, proximal body 610, and cable 650.

Shaft 620 of ultrasound device 600 is configured for trans-vaginal insertion into position adjacent to or in abutment with the cervix such that ultrasound sensor assembly 630 is oriented to enable ultrasound imaging of e.g., the cervix, uterus, and surrounding tissue. More specifically, distal end portion 624 of shaft 620 includes ultrasound sensor assembly 630. Ultrasound sensor assembly 630 includes one or more ultrasound sensors 632 oriented towards a distal surface 672 of distal end portion 624 of shaft 620 such that ultrasound sensor assembly 630 can be utilized for imaging e.g., the cervix, uterus, and surrounding tissue. Ultrasound sensor assembly 630 may be configured for 2D and/or 3D imaging. Distal surface 672 may define a bulbous configuration or any other configuration, e.g., such as those detailed with respect to the above ultrasound devices, to facilitate ultrasound imaging.

Shaft 620 of ultrasound device 600 further defines a hollow section 626 defined by a pair of spaced-apart sidewalls 627 and open top and bottom sides. Hollow section 626 of shaft 620 is configured to receive movable sheath 660 therein. A coupling mechanism 680 couples movable sheath 660 with shaft 620 to enable movable sheath 660 to move between an in-line position, wherein movable sheath 660 is substantially (e.g., +/−10%) disposed within hollow section 626 of shaft 620 and is substantially coaxial with shaft 620, and an angled position, wherein the longitudinal axes of shaft 620 and movable sheath 660 are disposed at angles relative to one another such that movable sheath 660 extends from hollow section 626 of shaft 620. In the in-line position, movable sheath 660 may be fully disposed within an outer annular dimension of shaft 620 (e.g., a maximum, minimum, or other outer annular dimension in embodiments where multiple dimensions are provided) so as not to protrude therefrom. Alternatively, movable sheath 660 may extend radially outwardly from an outer annular dimension of shaft 620 in the in-line position; in such embodiments, movable sheath 660, in the in-line position protrudes, radially outwardly a minimal amount from shaft 620 as compared to movable sheath 660 in angled positions.

Coupling mechanism 680 may include, for example, a pin-aperture connection to enable pivoting of movable sheath 660 relative to shaft 620 while remaining longitudinally fixed. Alternatively, as illustrated, coupling mechanism 680 may include a pin-slot connection including one or more pins 682 engaged with one of shaft 620 or movable sheath 660 (e.g., a pair of pins 682 extending radially outwardly from movable sheath 660 in opposite directions), and one or more slots 684 receiving the one or more pins 682 and defined within the other of shaft 620 or movable sheath 660 (e.g., a slot 684 defined within each sidewall 627). In this manner, movable sheath 660 may slide longitudinally and pivot relative to shaft 620 between the in-line and angled positions. Other suitable coupling mechanisms 680 are also contemplated.

Movable sheath 660 may be moved, e.g., pivoted and/or translated, relative to shaft 620 via coupling mechanism 680 locally, e.g., via manipulation of movable sheath 660 itself, or remotely, e.g., via manipulation of one or more remote actuators (not shown), e.g., disposed on proximal body 610, and associated drive components (not shown), e.g., shafts, cables, linkages, etc. interconnecting the remote actuators with coupling mechanism 680. Further, movement of movable sheath 660 relative to shaft 620 via coupling mechanism 680 may be manual or powered, e.g., via one or more motors (not shown) disposed within proximal body 610 or otherwise positioned.

Movable sheath 660 defines a longitudinal lumen 662 extending longitudinally therethrough that is sufficient to enable passage of at least a portion of an endoscope device e.g., elongated tubular member 202 of hysteroscope 200, therethrough such that a distal portion of the elongated tubular member 202 extends through an open distal end 664 of longitudinal lumen 662 and distally from movable sheath 660. Longitudinal lumen 662 may additionally or alternatively be configured to permit passage of other instrumentation, e.g., one or more working instruments, therethrough. As an alternative to movable sheath 660 defining a linear configuration, movable sheath 660 may be curved in one or more directions or otherwise configured.

With particular reference to FIG. 7, in use, ultrasound device 600, with movable sheath 660 disposed in the in-line position, is inserted trans-vaginally through the vaginal canal "V" such that distal end portion 624 of shaft 620 thereof is disposed adjacent or in abutment with the cervix "C." In this position, more specifically, ultrasound sensor assembly 630 is positioned adjacent or in abutment with the cervix "C" to enable ultrasound imaging of the uterus "U" and surrounding tissue. With shaft 620 in this position, movable sheath 660 may be moved, e.g., pivoted and/or slid, relative to shaft 620 such that open distal end 664 of longitudinal lumen 662 is oriented towards and/or extends through the cervix "C." In this orientation, elongated tubular member 202 of hysteroscope 200 may be inserted through movable sheath 660, through the cervix "C," and into the uterus "U" whereby hysteroscope 200 may be utilized for visualization within the uterus "U," together with or separately from the ultrasound imaging. Hysteroscope 200 may also be used for the introduction of fluid into and/or the removal of fluid from the uterus "U" and/or for passage of a working instrument 100, e.g., a tissue resection device, ablation device, biopsy device, etc., therethrough and into the uterus "U" to perform one or more hysteroscopic tasks therein (e.g., within the uterus "U") or therethrough (e.g., within the uterine wall). The movable configuration of sheath 660 relative to shaft 620 allows for ultrasound sensor assembly 630 to be positioned in a first orientation to facilitate ultrasound imaging and for sheath 660 (and, thus, hysteroscope 200, working instrument 100, or other instrumentation inserted therethrough) to be oriented in a second, different, selectable direction for passage into the uterus "U" to perform one or more surgical tasks therein.

Figure 8:
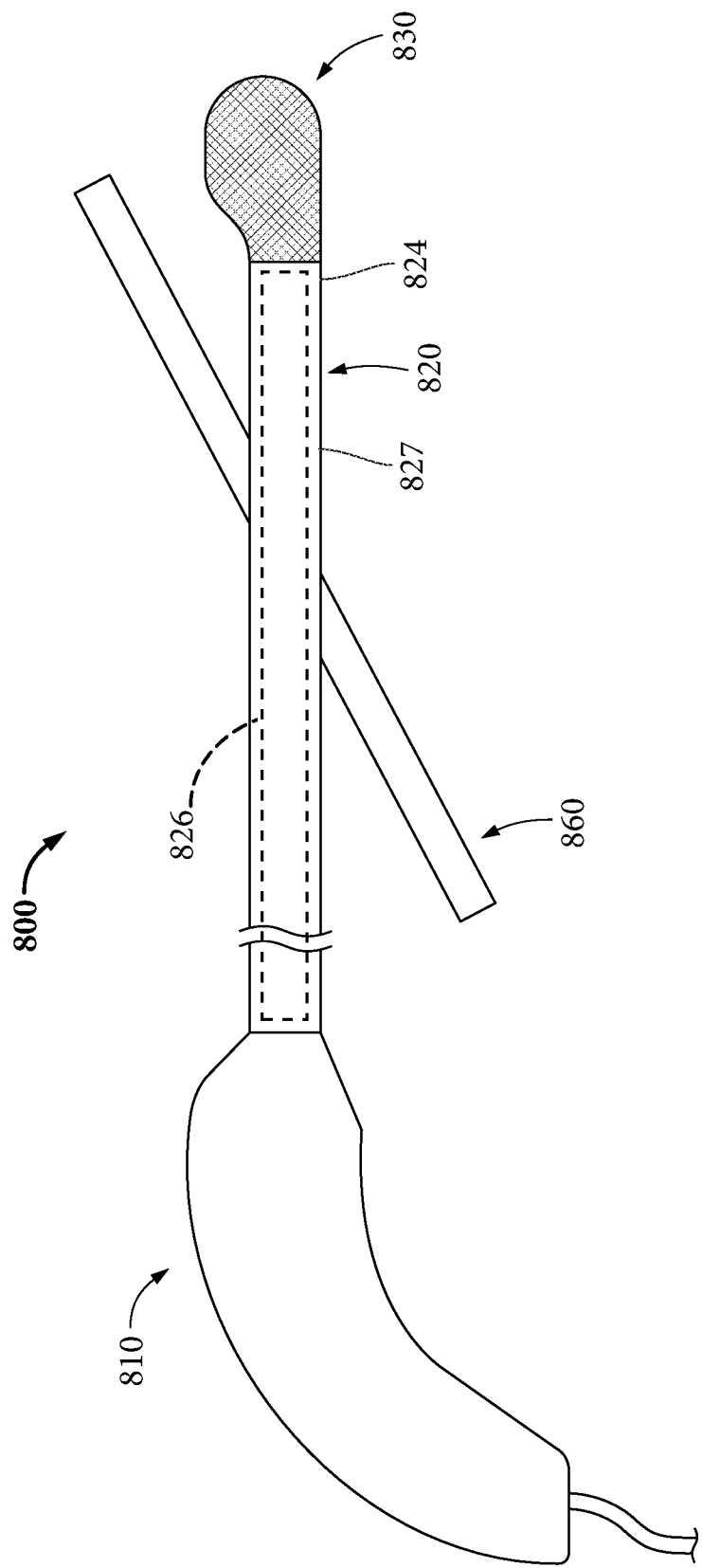
FIG. 8 is a side view of another ultrasound device configured for use with the hysteroscopy system of FIG. 1.

Turning to FIG. 8, another ultrasound device 800 is provided in accordance with the present disclosure. Ultrasound device 800 is similar to ultrasound device 600 (FIGS. 6 and 7) and, thus, only differences therebetween are described in detail below. Ultrasound device 800 includes a proximal body 810, a shaft 820 extending distally from proximal body 810, and an ultrasound sensor assembly 830 disposed at a distal end portion 824 of shaft 820.

Shaft 820 of ultrasound device 800 is configured for trans-vaginal insertion into position adjacent to or in abutment with the cervix such that ultrasound sensor assembly 830 is oriented to enable ultrasound imaging of e.g., the cervix, uterus, and surrounding tissue. Shaft 820 of ultrasound device 800 defines a hollow section 826 defined by a pair of spaced-apart sidewalls 827 and open top and bottom sides. Hollow section 826 of shaft 820 may extend along a portion of a length of shaft 820 or substantially the entire length of shaft 820.

Hollow section 826 is configured to removably receive one or more surgical instruments 860, e.g., a sheath, a hysteroscope, a tissue resection device, an ablation device, a biopsy device, or other suitable surgical instrument(s) side-by-side relative to one another or telescopically relative to one another. More specifically, sidewalls 827 disposed on either side of hollow section 826 guide insertion, longitudinal sliding, and/or pivoting of the one or more surgical instruments 860 relative to shaft 620 similarly as detailed above with respect to ultrasound device 600 (FIGS. 6 and 7), while also allow for interchangeable use of different surgical instruments 860. That is, ultrasound device 800 does not include a coupling mechanism like ultrasound device 600 (FIGS. 6 and 7) and, thus, surgical instruments 860 are removably receivable within hollow section 826 of shaft 820.

Referring to FIGS. 9 and 10A-10C, another ultrasound device provided in accordance with the present disclosure is shown generally identified by reference numeral 900 including hysteroscope 200 operably inserted therethrough. Except as explicitly contradicted below, ultrasound device 900 may include any of the features of the ultrasound devices detailed above.

Ultrasound device 900 includes a frame 902 and an ultrasound sensor assembly 930. Frame 902 is formed from a pair of spaced-apart rails 904. Rails 904 may be configured as plates extending in substantially parallel orientation relative to one another, or in any other suitable manner. Rails 904 are bent at a bend 906 to define a more-proximal upright portion 910 and a more-distal longitudinal portion 920 disposed at an angle relative to one another. The angle may be, in configurations, from about 60 degrees to about 120 degrees, in other configurations, from about 75 degrees to about 105 degrees, and in yet other configurations, about 90 degrees. A proximal spacer 912 is disposed between the rails 904 at upright portion 910, e.g., at the proximal end portion of upright portion 910, of frame 902 and is secured therebetween, e.g., via pins, bolts, adhesive, overmolding, or in any other suitable manner, such that rails 904 are secured to one another and the spacing therebetween along upright portion 910 is maintained. A distal spacer 922 is disposed between the rails 904 at longitudinal portion 920, e.g., at the distal end portion of longitudinal portion 920, of frame 902 and is secured therebetween, e.g., via pins, bolts, adhesive, overmolding, or in any other suitable manner, such that rails 904 are secured to one another and the spacing therebetween along longitudinal portion 920 is maintained. Additional or alternative spacers for similar purposes are also contemplated.

The proximal end portion of upright portion 910 of frame 902 may include a handle (e.g., similar to any of the above configurations) disposed thereon to facilitate manual manipulation of ultrasound device 900 and/or may be configured to be mounted on a support arm "SA" of a support device "SD," e.g., a robotic arm of a surgical system (see FIG. 20) or a mounting arm of a mounting frame, thus obviating the need for a surgeon to manually manipulate ultrasound device 900 and/or manually hold ultrasound device 900 to retain the position thereof. Suitable mounting hardware "M" may be provided integrally with or attachable to the proximal end portion of upright portion 910 for the purpose of releasably engaging support arm "SA."

Ultrasound sensor assembly 930 extends distally from the distal end of longitudinal portion 920 of frame 902 and is secured thereto. More specifically, ultrasound sensor assembly 930 may be formed with, attached to, or otherwise fixed relative to distal spacer 922 such that the engagement of distal spacer 922 between rails 904 also secures ultrasound sensor assembly 930 relative to frame 902, or may be secured relative to frame 902, directly or indirectly, in any other suitable manner. Ultrasound sensor assembly 930 includes one or more ultrasound sensors 932, e.g., ultrasound transducers, to enable ultrasound imaging of tissue, e.g., the uterus, and, more specifically, to enable 2D and/or 3D ultrasound imaging. The field of view produced by ultrasound sensor assembly 930 may be from about 90 degrees to about 180 degrees, in other configurations from about 120 degrees to about 150 degrees. Ultrasound sensor assembly 930 may be oriented such that a longitudinal axis defined by longitudinal portion 920 of frame 902 extends through the field of view, extends along a boundary line of the field of view, or is offset from the field of view. In aspects, ultrasound sensor assembly 930 is orientated such that a center line extending from the ultrasound sensor assembly 930 and bisecting the field of view is disposed at an oblique angle (in some aspects, an acute angle) relative to the longitudinal axis defined by longitudinal portion 920 of frame 902. The other ultrasound devices may similarly be configured, e.g., wherein the ultrasound imaging field of view is disposed at an oblique angle (in some aspects, an acute angle) relative to the frame or shaft of the ultrasound device.

Continuing with reference to FIGS. 9 and 10A-10C, bend 906 of frame 902 enables insertion of elongated tubular member 202 of hysteroscope 200 between rails 904 in substantially coaxial or parallel orientation relative to the longitudinal axis defined by longitudinal portion 920 of frame 902. Alternatively, elongated tubular member 202 of hysteroscope 200 may be inserted between rails 904 at an angle relative to the longitudinal axis. Regardless of the angle of insertion, with elongated tubular member 202 of hysteroscope 200 extending between rails 904, rails 904 serve to substantially inhibit transverse movement (sliding or tilting) of elongated tubular member 202 relative to the longitudinal axis defined by longitudinal portion 920 of frame 902 while permitting vertical movement (sliding and tilting), axial rotation, and axial sliding of elongated tubular member 202 relative to the longitudinal axis defined by longitudinal portion 920 of frame 902.

Figure 9:
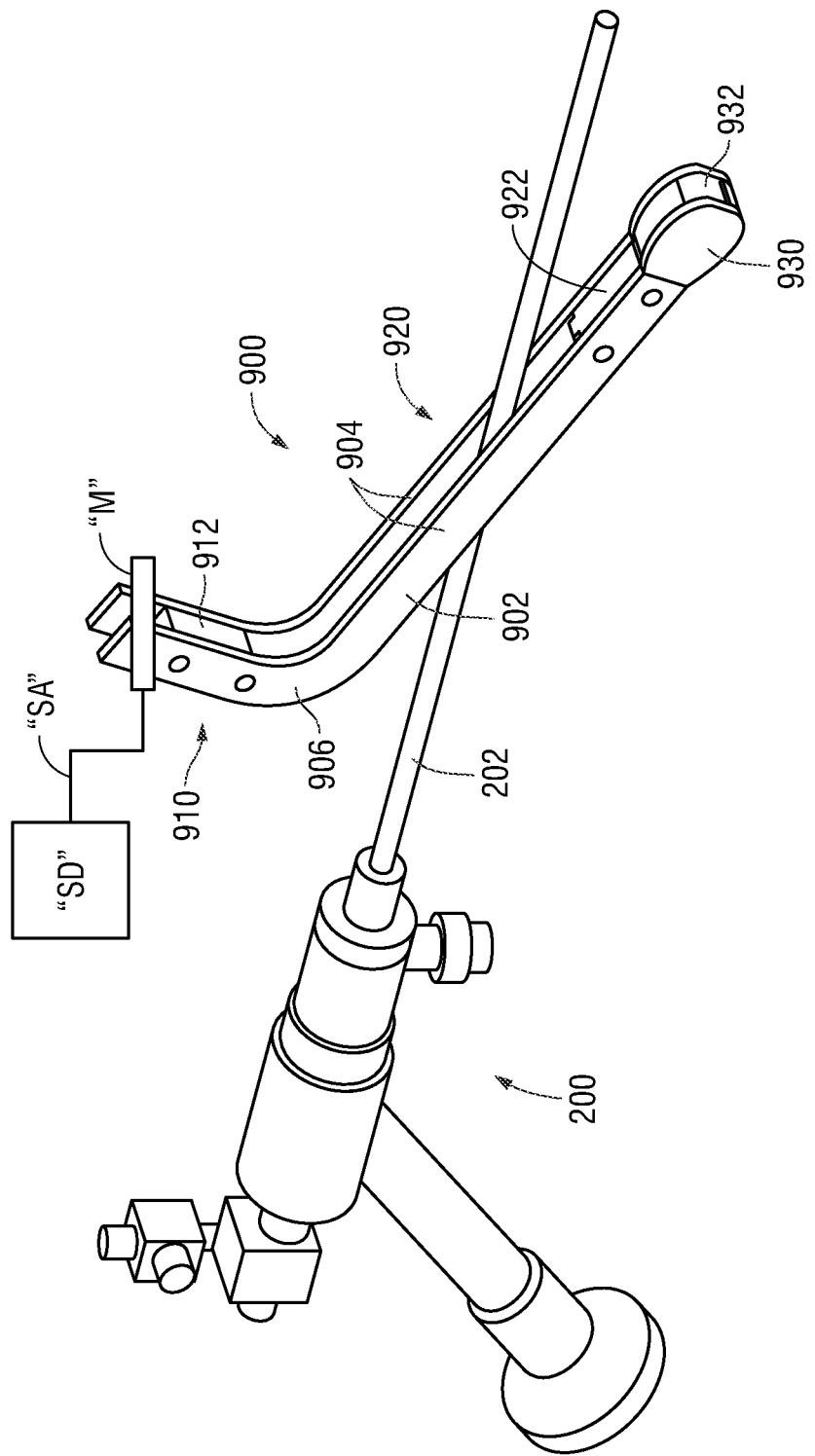
FIG. 9 is a perspective view of another ultrasound device including a hysteroscope operably received therein.
Figure 10A:
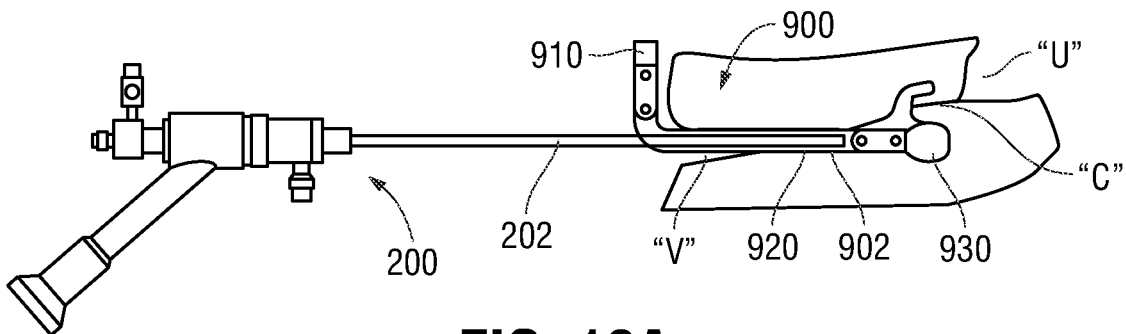
FIGS. 10A-10C are perspective views illustrating the ultrasound device of FIG. 9 positioned adjacent the cervix and progressive insertion of the hysteroscope of FIG. 9 through the cervix and into the uterus.
Figure 10B:
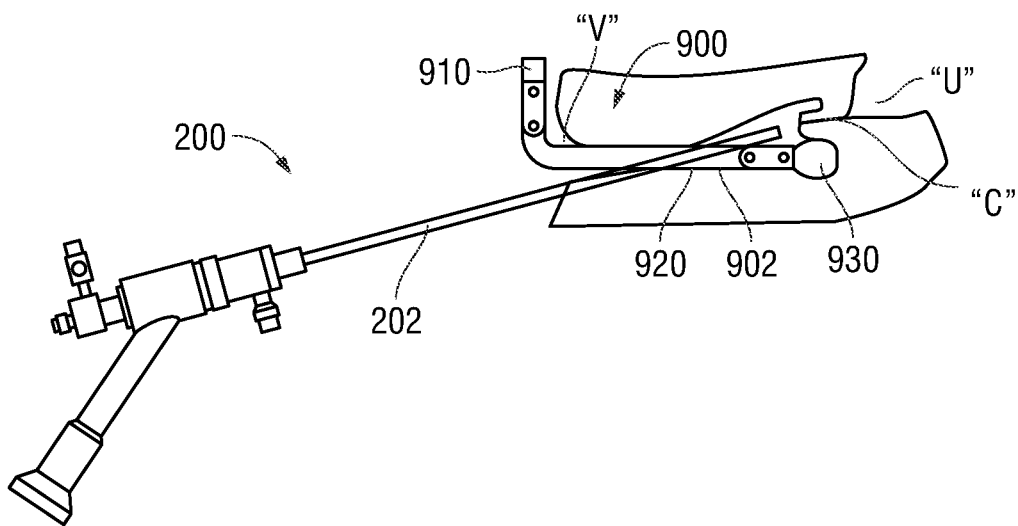
Figure 10C:
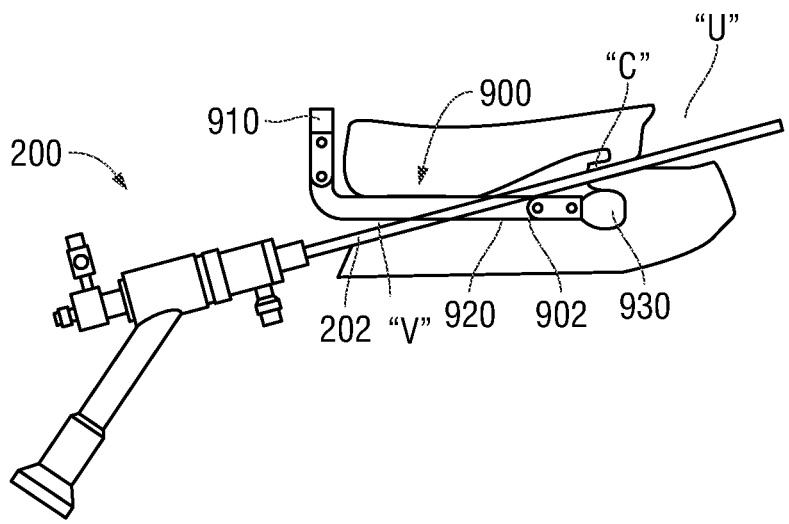

With reference to FIGS. 10A-10C, and initially to FIG. 10A, in use, longitudinal portion 920 of frame 902 of ultrasound device 900 may first be inserted trans-vaginally through the vaginal canal "V" such that ultrasound sensor assembly 930 is positioned adjacent or in abutment with the cervix "C" to enable ultrasound imaging of the uterus "U" and surrounding tissue, while upright portion 910 remains externally disposed, e.g., for manual manipulation or fixing to a support arm "SA" (see FIG. 9). Elongated tubular member 202 of hysteroscope 200 may then be inserted between rails 904 (FIG. 9) in substantially coaxial or parallel orientation relative to the longitudinal axis defined by longitudinal portion 920 of frame 902, although other suitable insertion orientations are also contemplated. Alternatively, elongated tubular member 902 may be positioned between rails 904 in substantially coaxial or parallel orientation relative to the longitudinal axis defined by longitudinal portion 920 of frame 902 prior to insertion and may be inserted in conjunction with longitudinal portion 920 of frame 902. Inserting elongated tubular member 202 of hysteroscope 200 in either of these manners substantially reduces the required insertion force and discomfort to the patient since elongated tubular member 202 is disposed within frame 902 and, thus, does not substantially interact with tissue at this point.

Referring to FIG. 10B, with ultrasound device 900 and hysteroscope 200 inserted as detailed above, hysteroscope 200 may be manipulated relative to ultrasound device 900 to position elongated tubular member 202 for insertion through the cervix "C" and into the uterus "U." This may be accomplished, for example, via vertically tilting elongated tubular member 202 relative to frame 902 until a distal end of elongated tubular member 202 is substantially aligned with the cervix "C." The ultrasound images provided by ultrasound device 900 may be utilized to confirm proper orientation of elongated tubular member 202.

Turning to FIG. 10C, with elongated tubular member 202 orientated as detailed above, elongated tubular member 202 may be slid distally (maintaining the orientation thereof) relative to frame 902 such that the distal end of elongated tubular member 202 extends through the cervix "C" and into the uterus "U," under the guidance of the ultrasound imaging provided by ultrasound device 900. One or more surgical tasks, e.g., visualization, tissue resection, ablation, biopsy, etc., may then be performed within the uterus "U" via hysteroscope 200 or a working instrument 100 (FIG. 1) inserted therethrough, all under the guidance of the ultrasound imaging provided by ultrasound device 900.

With reference to FIGS. 11A-11D, in conjunction with FIG. 9, as detailed above, with elongated tubular member 202 of hysteroscope 200 extending between rails 904 of ultrasound device 900, rails 904 serve to substantially inhibit lateral movement of elongated tubular member 202 relative to the longitudinal axis defined by longitudinal portion 920 of frame 902 while permitting vertical movement and axial movement (sliding and rotation) of elongated tubular member 202 relative to the longitudinal axis defined by longitudinal portion 920 of frame 902. Thus, hysteroscope 200 has plural degrees of freedom relative to ultrasound device 900. In some situations, however, it may be desirable to selectively lock hysteroscope 200 relative to ultrasound device 900, e.g., once a desired position and orientation is achieved. More specifically, a locking mechanism 1100 may be provided for selectively locking hysteroscope 200 relative to ultrasound device 900 at any suitable position and orientation.

Locking mechanism 1100 is disposed between rails 904 of longitudinal portion 920 of frame 902 of ultrasound device 900 and includes a pair of clamp brackets 1110, a resilient sling 1120 extending between lower ends 1112a of the clamp brackets 1110, an engagement pin 1130 extending outwardly from each clamp bracket 1110, and a cam screw assembly 1140 including a screw 1142 and a cam lock lever 1144. Resilient sling 1120 is formed from a resilient material configured to resiliently resist stretching of sling 1120 from either or both ends 1122 thereof.

Each clamp bracket 1110 is disposed adjacent one of the rails 904 on an inwardly-facing surface thereof, towards a proximal end of longitudinal portion 920 of frame 902, although other positions and/or configurations are also contemplated. As noted above, resilient sling 1120 extends between lower ends 1112a of clamp brackets 1110, towards the distal ends thereof. A support bar 1114 extends proximally from each clamp bracket 1110. Either or both support bars 1114 defines a threaded connector 1116 at the free proximal end portion thereof. In other configurations, support bars 1114 are omitted and a threaded connector 1116 is defined or disposed on either or both clamp brackets 1110. Threaded connector(s) 1116 may be a threaded portion(s) of support bar(s) 1114, support bar(s) 1114 itself, a male or female threaded component(s) attached to support bar(s) 1114, or any other suitable threaded component(s). In configurations where only one threaded connector 1116 is provided, the other support bar 1114 may include a non-threaded connector, e.g., a rotatable connector.

Engagement pins 1130 extend outwardly from clamp brackets 1110 into wells 1132 defined within the interior surfaces of rails 904. Alternatively, engagement pins 1130 may extend outwardly from clamp brackets 1110 into elongated channels defined within and extending longitudinally along the interior surfaces of longitudinal portion 920 of frame 902 such that, in an unlocked condition, locking mechanism 1100 may be translated longitudinally along longitudinal portion 920 of frame 902.

Continuing with reference to FIGS. 11A-11D, in conjunction with FIG. 9, cam screw assembly 1140 includes, as noted above, a screw 1142 and a cam lock lever 1144. Screw 1142 may be disposed atop one or both rails 904 of longitudinal portion 920 of frame 902 or may extend through apertures or longitudinal slots defined within one or both rails 904 of longitudinal portion 920 of frame 902. In either configuration, screw 1142 extends transversely relative to rails 904 and is threadingly engaged with threaded connector(s) 1116 of support bar(s) 1114. In configurations where both support bars 1114 include threaded connectors 1116, screw 1142 is threadingly engaged with each of the threaded connectors 1116 in an opposite manner, e.g., one via a right-handed threaded engagement and the other via a left-handed threaded engagement. In configurations where only one support bar 1114 includes a threaded connector 1116, the non-threaded connector of the other support bar 1114 may rotatably and/or slidably receive screw 1142.

End stop washers 1146 are disposed towards the opposed ends of screw 1142 such that threaded connector(s) 1116 (and the non-threaded connector, if provided) are disposed between end stop washers 1146. End stop washers 1146 are axially fixed on screw 1142 and may be rotatable or rotatably fixed relative to screw 1142. In configurations where screw 1142 extends through an aperture or slot defined within one or both of the rails 904 of longitudinal portion 920 of frame 902, one or both of the end stop washers 1146 may be disposed outwardly of the adjacent rail 904.

Cam lock lever 1144 is pivotably coupled to an end portion of screw 1142, outwardly adjacent one of the end stop washers 1146, via a pivot 1148. Cam lock lever 1144 is positioned outwardly of the rails 904 of longitudinal portion 920 of frame 902 to enable manual manipulation thereof by a user. Cam lock lever 1144 defines a cam surface 1145 that extends eccentrically about pivot 1148 such that in an unlocked position of cam lock lever 1144, cam surface 1145 is displaced from the adjacent end stop washer 1146, corresponding to an unlocked condition of cam lock mechanism 1140 wherein screw 1142 is rotatable (see FIG. 11C), and such that in locked position of cam lock lever 1144, a second, cam surface 1145 is urged into contact with the adjacent end stop washer 1146 to apply a force thereto, corresponding to a locked condition of cam lock mechanism 1140 wherein screw 1142 is inhibited from rotation (see FIG. 11D). Cam lock lever 1144 is pivotable about pivot 1148 between the unlocked and locked positions thereof.

Figure 11A:
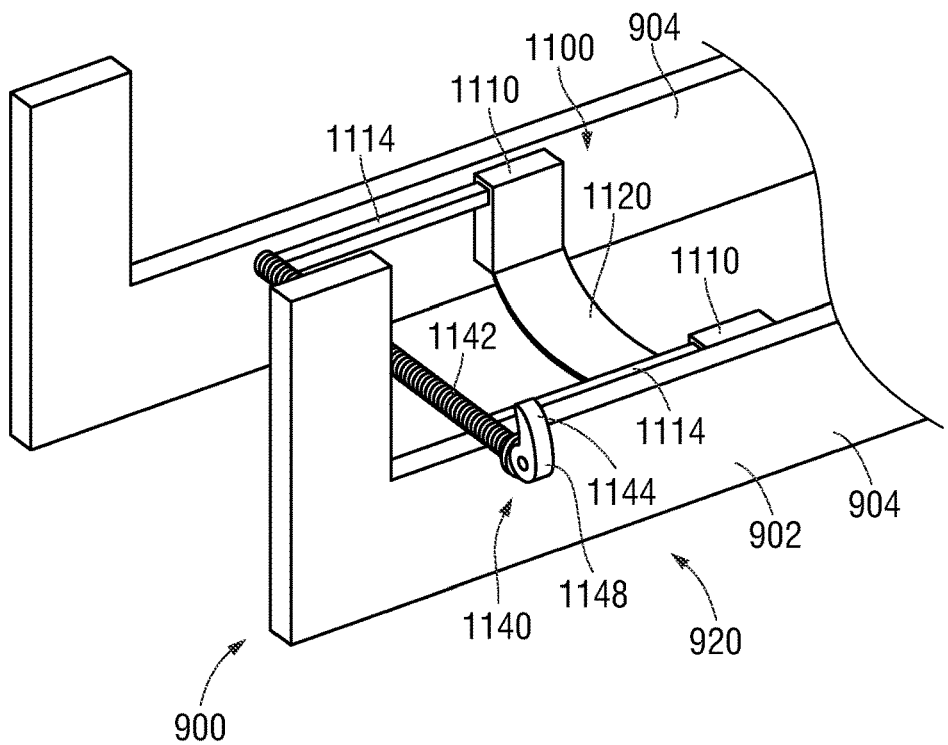
FIG. 11A is a perspective view of a proximal end portion of the ultrasound device of FIG. 9 including a locking mechanism.
Figure 11B:
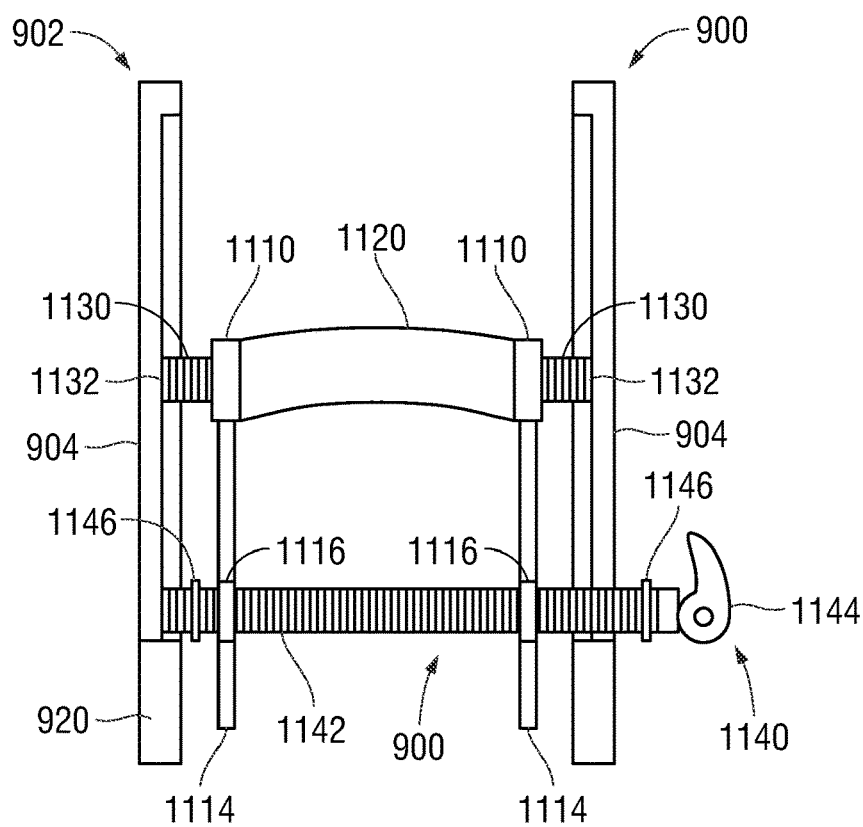
FIG. 11B is a top view of the proximal portion of the ultrasound device of FIG. 9 including the locking mechanism of FIG. 11A.
Figure 11C:
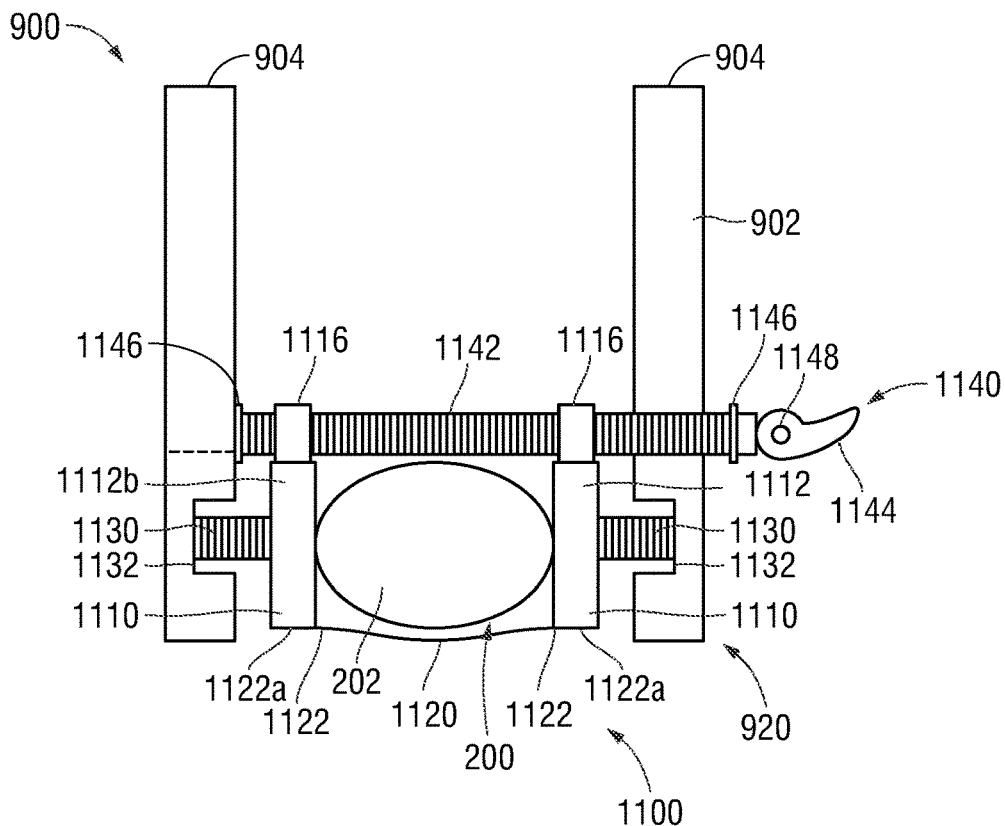
FIGS. 11C and 11D are proximal end views of the ultrasound device of FIG. 9 including the locking mechanism of FIG. 11A and including a hysteroscope operably received therein in unlocked and locked conditions, respectively.
Figure 11D:
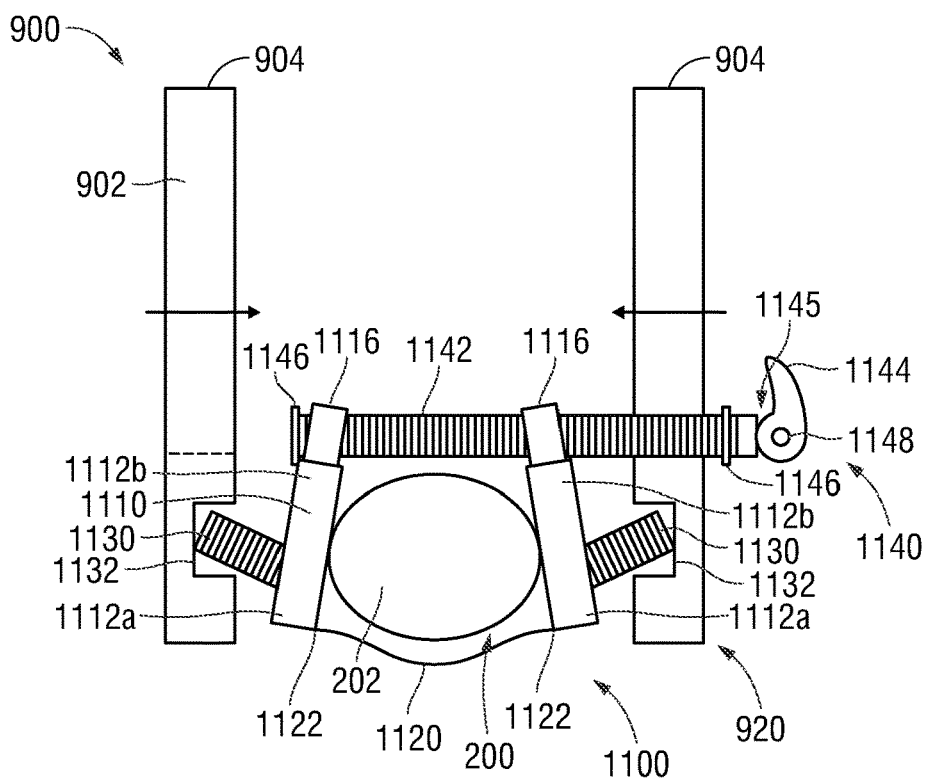

Referring to FIGS. 11C and 11D, in use, with longitudinal portion 920 of frame 902 of ultrasound device 900 inserted into position as detailed above (see FIG. 10A), elongated tubular member 202 of hysteroscope 200 may then be inserted between rails 904 of frame 902 and, more specifically, transversely between clamp brackets 1110 of locking mechanism 1100 and vertically between screw 1142 and sling 1120 of locking mechanism 1100. As shown in FIG. 11C, at this point, locking mechanism 1100 is disposed in the unlocked condition, allowing the insertion of elongated tubular member 202 therethrough and manipulation of elongated tubular member 202 therein to achieve a desired orientation and position. Alternatively, elongated tubular member 902 may be positioned between rails 904 and within locking mechanism 1100 prior to insertion and may be inserted in conjunction with longitudinal portion 920 of frame 902. In either configuration, once ultrasound device 900 is positioned as desired, elongated tubular member 202 may be manipulated, e.g., advanced distally, rotated, and or vertically tilted, relative to ultrasound device 900, e.g., to enable the distal end of elongated tubular member 202 to be inserted through the cervix "C" and into the uterus "U" to a desired position and orientation therein (see FIGS. 10B and 10C). Locking mechanism 1100, being in the unlocked condition, allows such advancement, rotation, and/or tilting of elongated tubular member 202.

Once the desired orientation and position of elongated tubular member 202 is achieved, locking mechanism 1100 may be transitioned to the locked condition to thereby lock elongated tubular member 202 in the desired orientation and position relative to ultrasound device 900. In order to transition locking mechanism 1100 to the locked condition, screw 1142 is rotated about its axis to move one or both of support bars 1114 (depending upon whether one or both of the support bars 1114 includes a threaded connector 1116) towards the other support bar 1114, thereby pulling the upper ends 1112b of one or both of clamp brackets 1110 towards one another to clamp in engagement about elongated tubular member 202 from opposing sides thereof, thus fixing elongated tubular member 202 relative to lock mechanism 1100. As the upper ends 1112b of one or both of clamp brackets 1110 are moved towards one another, the lower ends 1112a of the one or both clamp brackets 1110 are moved apart from one another, resiliently stretching sling 1120 from opposing ends thereof against the bias of sling 1120. In this manner, the rotation of screw 1142 together with the configuration of sling 1120 tilts clamp brackets 1110 from a generally parallel orientation relative to rails 904 of frame 902 and one another, to an angled orientation relative to rails 904 of frame 902 and one another, wherein upper ends 1112b of clamp brackets 1110 are in relatively closer approximation while lower ends 1112a are relatively farther apart. This tilting of clamp brackets 1110 relative to rails 904 of frame 902 causes engagement pins 1130 to angle within and relative to wells 1132 such that engagement pins 1130 are jammed within wells 1132, thereby fixing engagement pins 1130, clamp brackets 1110 and, thus, elongated tubular member 202 relative to rails 904 of frame 902.

Once the above-detailed fixing of elongated tubular member 202, locking mechanism 1100, and ultrasound device 900 relative to one another is achieved, cam lock lever 1144 may be pivoted from the unlocked position to the locked position to apply force against the adjacent end stop washer 1146 and thereby secure locking mechanism 1100 in the locked condition wherein elongated tubular member 202 is maintained in the desired orientation and position relative to ultrasound device 900. Accordingly, the need to manually maintain (or utilize a fixture or other tool to maintain) elongated tubular member 202 in fixed orientation and position relative to ultrasound device 900 is obviated. Referring additionally to FIGS. 1 and 10C, in this locked condition, a working instrument 100 may be inserted through hysteroscope 200 (if not already inserted therethrough) and into the uterus "U" and manipulated therein to perform one or more surgical tasks, all under the guidance of the ultrasound imaging provided by ultrasound device 900.

Continuing with reference to FIGS. 11C and 11D, in order to unlock locking mechanism, e.g., to enable removal of hysteroscope 200, cam lock lever 1144 is pivoted from the locked position back to the unlocked position and, thereafter, screw 1142 is rotated in the opposite direction to dislodge engagement pins 1130 from jammed engagement within wells 1132, enable sling 1120 to resilient return to its at-rest position, and release clamp brackets 1110 from engagement about elongated tubular member 202, thereby once again permitting relative movement, e.g., proximal or distal sliding, axial rotation, and/or vertical tilting, of elongated tubular member 202 relative to locking mechanism 1100 and ultrasound device 900.

Figure 12A:
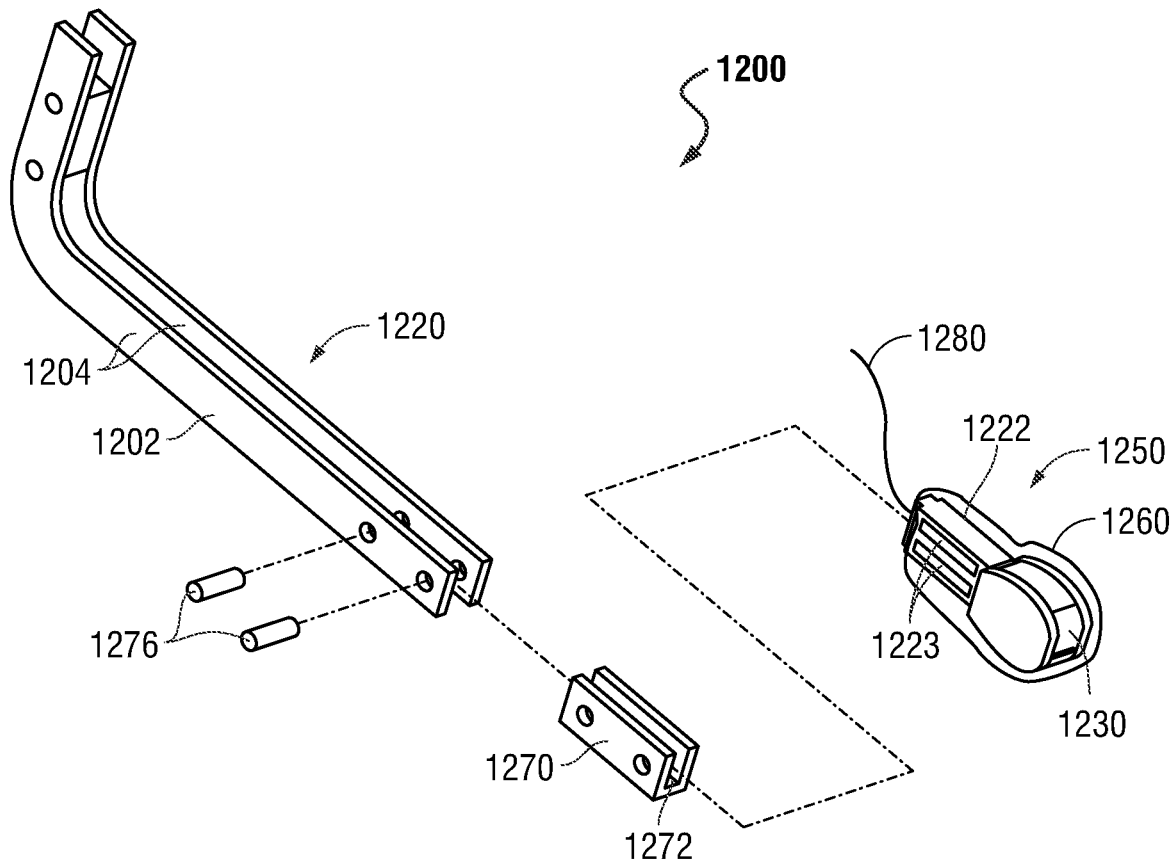
FIG. 12A is an exploded, perspective view of another ultrasound device in accordance with the present disclosure including a sterile barrier disposed over the ultrasound sensor assembly thereof.
Figure 12B:
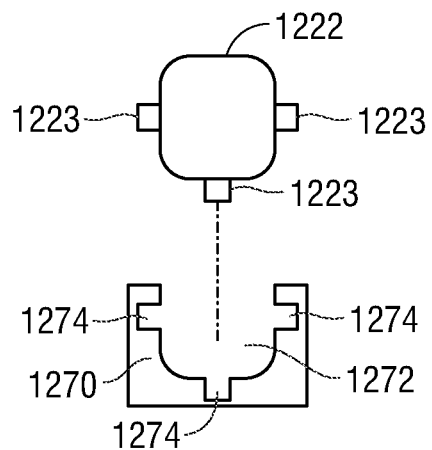
FIG. 12B is an exploded, transverse, cross-sectional view of adapter components of the ultrasound device of FIG. 12A.

Turning to FIGS. 12A and 12B, another ultrasound device provided in accordance with the present disclosure is shown generally identified by reference numeral 1200. Except as explicitly contradicted below, ultrasound device 1200 is similar to and may include any of the features of ultrasound device 900 (FIG. 9), detailed above. Thus, only differences between ultrasound device 1200 and ultrasound device 900 (FIG. 9) are described in detail below while similarities are summarily described or omitted entirely.

Ultrasound device 1200 includes removable assembly 1250 including an ultrasound sensor assembly 1230, a distal spacer 1222, a sterile barrier 1260, and an adapter 1270. Removable assembly 1250 further includes a connection cable 1280 housing one or more electrical wires enables connection of ultrasound sensor assembly 1230 to an ultrasound console (not shown). Ultrasound sensor assembly 1230 and distal spacer 1222 may be integrally formed as a unit, or distal spacer 1222 may be releasably engagable with ultrasound sensor assembly 1230. In either configuration, distal spacer 1222 defines engagement features 1223 on an exterior surface thereof such as, for example, an arrangement of fins protruding outwardly therefrom, although alternative or additional features, e.g., slots, are also contemplated. In configurations where distal spacer 1222 is releasably engagable with ultrasound sensor assembly 1230, various different ultrasound sensor assemblies 1230 and distal spacers 1222 corresponding thereto may be provided, enabling customization of ultrasound device 1200, e.g., to provide 2D ultrasound, 3D ultrasound, different sensor arrangements, etc.

Sterile barrier 1260 is configured to surround ultrasound sensor assembly 1230 and distal spacer 1222. Sterile barrier 1260 maintains ultrasound sensor assembly 1230 in a sterile condition throughout use thereof without comprising the functionality of ultrasound sensor assembly 1230.

Adapter 1270 defines an interior receiving area 1272 including complementary engagement features 1274, e.g., a complementary arrangement of slots, to engagement features 1223 of distal spacer 1222 to facilitate engagement therebetween. Interior receiving area 1272 of adapter 1270, more specifically, is configured to receive and engage distal spacer 1222 therein with sterile barrier 1260 therebetween to thereby seal the interior of sterile barrier 1260, thus maintaining the sterility of ultrasound sensor assembly 1230. In some configurations, set screws or other suitable additional engagement features may be provided to facilitate engagement of distal spacer 1222 with adapter 1270 and sealing of sterile barrier 1260 therebetween.

Adapter 1270 is engagable between rails 1204 of longitudinal portion 1220 of frame 1202, e.g., via a pair of pins 1276 on either side thereof (only one set of pins is illustrated) or other suitable releasably engagement mechanism, to thereby enable releasable securement of ultrasound sensor assembly 1230 to frame 1202 with sterile barrier 1260 sealed about ultrasound sensor assembly 1230.

Referring to FIGS. 13A-13D, a method of forming a sterile enclosure about an ultrasound sensor assembly 1330 of an ultrasound device 1300 is provided in accordance with the present disclosure. Ultrasound device 1300 is similar to and may include any of the features of ultrasound device 900 (FIG. 9), detailed above. Thus, only differences between ultrasound device 1200 and ultrasound device 900 (FIG. 9) are described in detail below while similarities are summarily described or omitted entirely.

Figure 13A:
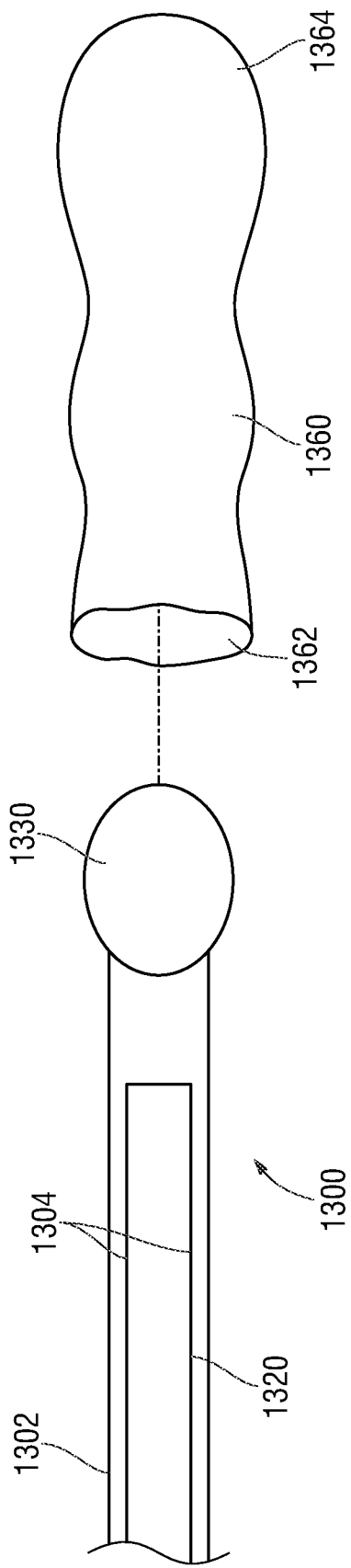
FIG. 13A-13D are top views progressively illustrating a method of sealing a sterile barrier over an ultrasound device.
Figure 13B:
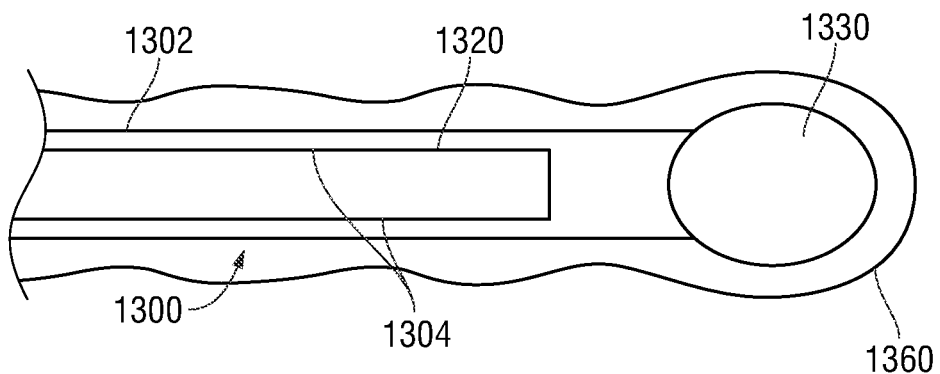

Initially, as shown in FIGS. 13A and 13B, a sterile barrier 1360 having an open end 1362 and a closer end 1364 is slid proximally, led by open end 1362 thereof, over ultrasound sensor assembly 1330 of ultrasound device 1300 and at least a portion of frame 1302 of ultrasound device 1300. Sterile barrier 1360 may surround and enclose the entirety of ultrasound device 1300 or a sufficient distal portion thereof so as to maintain sterility of ultrasound device 1300 during use. More specifically, in some configurations, sterile barrier 1360 surrounds and encloses at least a majority of longitudinal portion 1320 of frame 1302; in other configurations, sterile barrier 1360 surrounds and encloses longitudinal portion 1320 and at least a portion of the upright portion (not shown); in still other configurations, sterile barrier 1360 surrounds and encloses longitudinal portion 1320 and at least a majority of the upright portion; and in yet other configurations, sterile barrier 1360 surrounds and encloses the entire frame 1302.

Figure 13C:
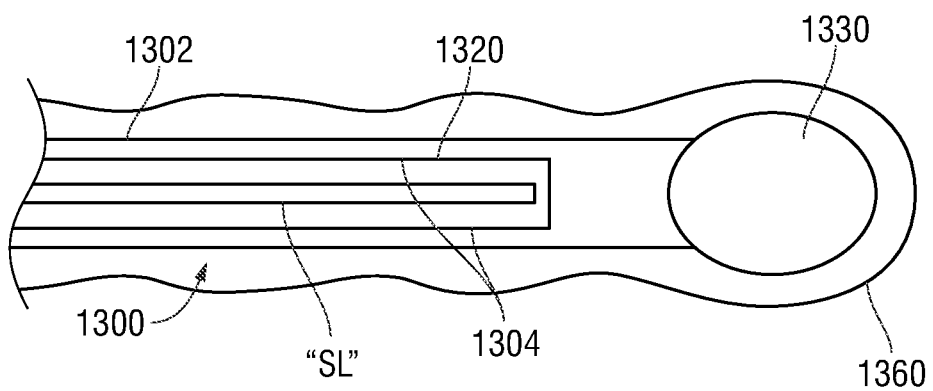
Figure 13D:
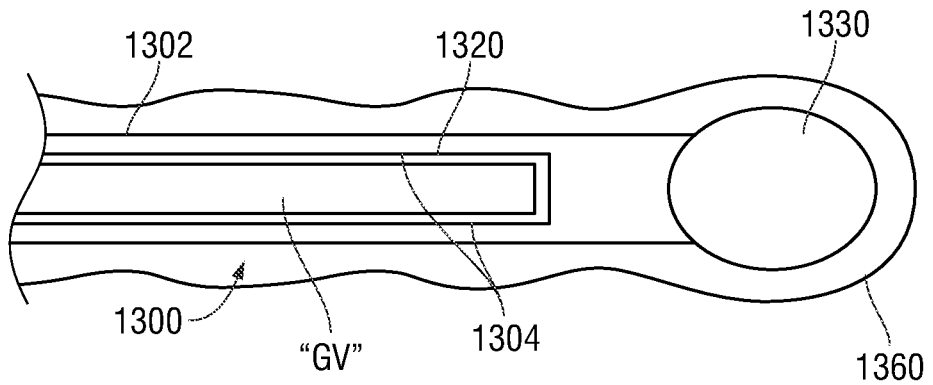

Referring to FIG. 13C, once sterile barrier 1360 is positioned as detailed above, the portions of sterile barrier 1360 extending transversely across the spaced-apart rails 1304 of frame 1302, e.g., across the top and bottom of longitudinal portion 1320 of frame 1302, are sealed along a seal line "SL," e.g., via heat sealing, ultrasonic sealing, or in any other suitable manner. With reference to FIG. 13D, once the seals are formed, or in simultaneous or overlapping temporal relation therewith, sterile barrier 1360 is cut along the seal line "SL," thereby defining a gap volume "GV" exposing the interior volume between the spaced-apart rails 1304 of longitudinal portion 1320 of frame 1302, while maintaining sterile barrier 1360 in sealed disposition about ultrasound sensor assembly 1330 and each of the of the rails 1304. Thus, a sealed barrier 1360 is formed to maintain ultrasound sensor assembly 1330 and at least portions of spaced-apart rails 1304 in a sterile condition throughout use of ultrasound device 1300, without compromising the ability of hysteroscope 200 (FIG. 9) to be inserted between spaced-apart rails 1304 and manipulated relative thereto.

Turning to FIGS. 14A-16, still another ultrasound device provided in accordance with the present disclosure and configured to enable sterile sealing of the ultrasound sensor assembly thereof to maintain sterility during use is shown generally identified by reference numeral 1400. Ultrasound device 1400 is similar to and may include any of the features of ultrasound device 900 (FIG. 9), detailed above. Thus, only differences between ultrasound device 1400 and ultrasound device 900 (FIG. 9) are described in detail below while similarities are summarily described or omitted entirely.

Figure 14A:
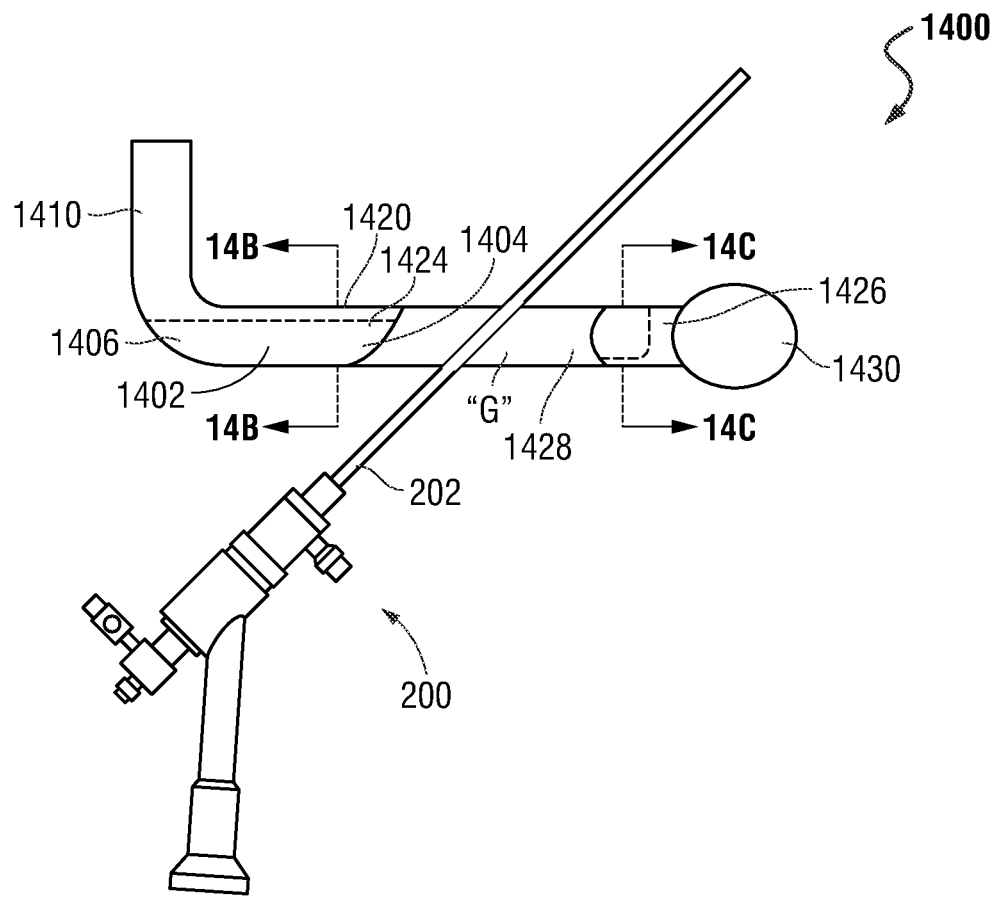
FIG. 14A is a side view of still another ultrasound device in accordance with the present disclosure including a hysteroscope operably received therein.
Figure 14B:
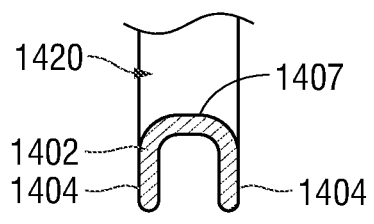
FIGS. 14B and 14C are transverse, cross-sectional views taken across section lines "14B-14B" and "14C-14C," respectively, of FIG. 14A.
Figure 14C:
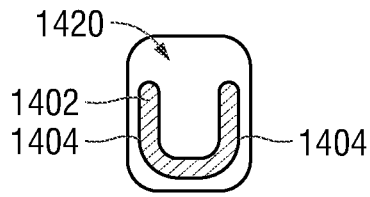

Referring to FIGS. 14A-14C, ultrasound device 1400 includes a frame 1402 formed from a pair of spaced-apart rails 1404, and an ultrasound sensor assembly 1430 disposed at a distal end portion of frame 1402. Rails 1404 are bent at a bend 1406 to define a more-proximal upright portion 1410 and a more-distal longitudinal portion 1420. Longitudinal portion 1420 defines a proximal section 1424, a distal section 1426, and a connector section 1428 disposed between proximal and distal sections 1424, 1426, respectively. Rails 1404 are interconnected via a first backspan 1407 extending across upper ends thereof along proximal section 1424 of longitudinal portion 1420 such that proximal section 1424 of longitudinal portion 1420 defines an upside down U-shaped configuration (see FIG. 14B), and are interconnected via a second backspan 1408 extending across lower ends thereof along distal section 1426 of longitudinal portion 1420 such that distal section 1426 of longitudinal portion 1420 defines a U-shaped configuration (see FIG. 14C). Further, one of the rails 1404 is discontinuous in that it defines a gap "G" along connector section 1428 and, thus, does not extend along connector section 1428; rather, only one of the rails 1404 extends along connector section 1428 (see also FIG. 15).

Figure 15:
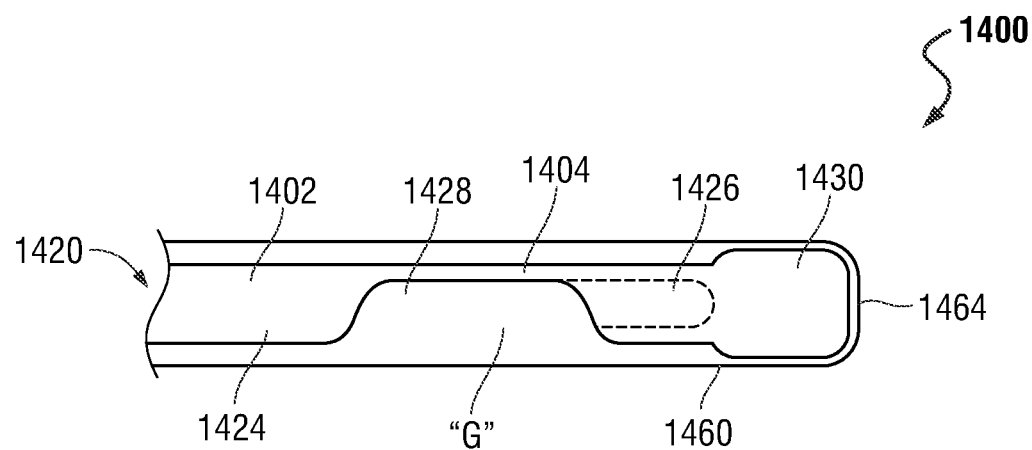
FIG. 15 is a side view of a distal portion of the ultrasound device of FIG. 14A including a sterile barrier disposed thereabout.
Figure 16:
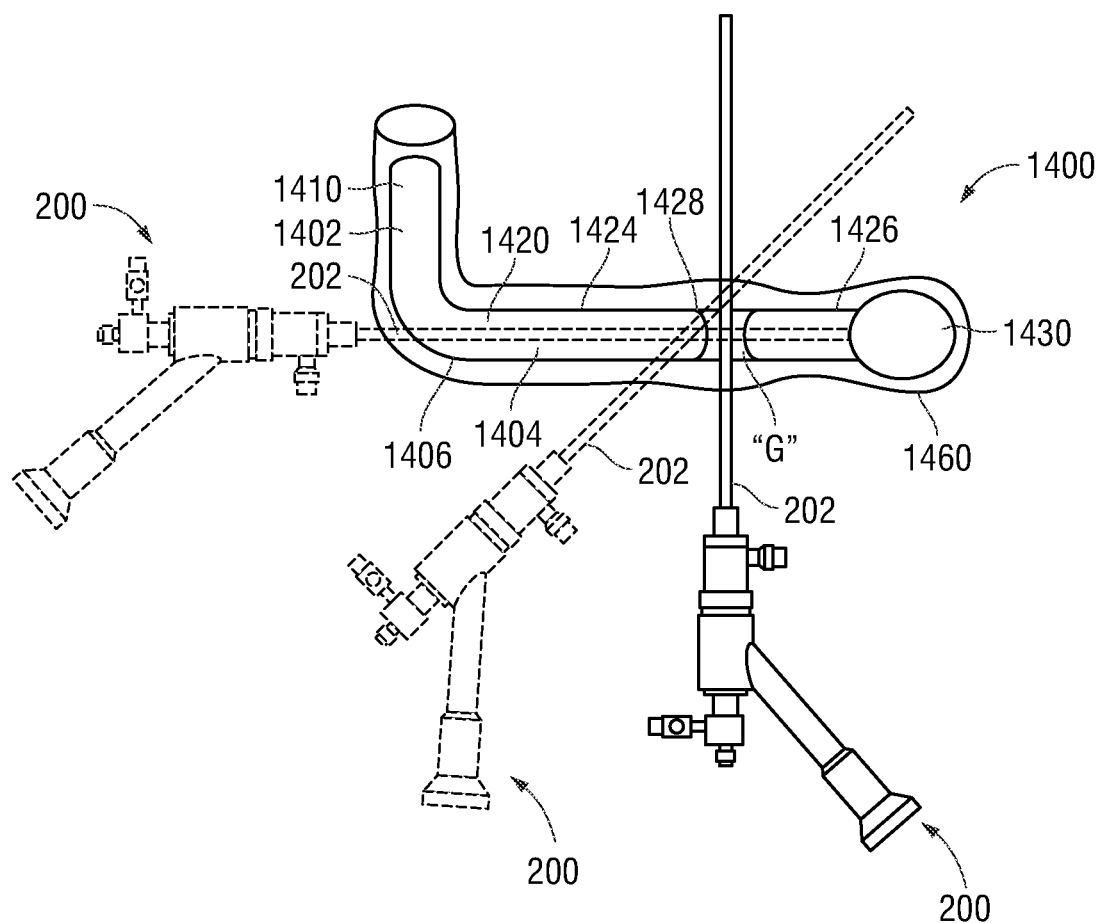
FIG. 16 is a side view of the ultrasound device of FIG. 14A including the sterile barrier disposed thereabout and the hysteroscope inserted and operably positioned relative thereto.

With additional reference to FIGS. 15 and 16, ultrasound device 1400 is configured to receive a sterile barrier 1460 that surrounds and encloses the entirety of ultrasound device 1400 or a sufficient distal portion thereof so as to maintain sterility of ultrasound device 1400 during use. More specifically, sterile barrier 1460 is configured to extend proximally from a closed distal end 1464 thereof about ultrasound sensor assembly 1430, about distal section 1426 of longitudinal portion 1420 of frame 1402, connector section 1428 of longitudinal portion 1420 of frame 1402, and at least a portion of proximal section 1424 of longitudinal portion 1420 of frame 1402.

Despite sterile barrier 1460 surrounding and enclosing ultrasound sensor assembly 1430 and at least a portion of longitudinal portion 1420 of frame 1402, hysteroscope 200 may still be operably coupled with ultrasound device 1400 without breaking the sterility of sterile barrier 1460, without compromising the functionality of ultrasound device 1400, and without compromising the functionality or maneuverability of hysteroscope 200 relative to ultrasound device 1400. More specifically, with reference to FIG. 16, in order to operably couple hysteroscope 200 with longitudinal portion 1420 of frame 1402, elongated tubular member 202 of hysteroscope 200 is first oriented in substantially perpendicular orientation relative to longitudinal portion 1420 of frame 1402 and is then moved transversely through gap "G" into connector section 1428 of longitudinal portion 1240 of frame 1402, between rails 104 thereof. Sterile barrier 1460 is flexed inwardly to permit this insertion of elongated tubular member 202 into frame 1402.

Once elongated tubular member 202 of hysteroscope 200 is disposed within connector section 1428 of longitudinal portion 1240 of frame 1402, elongated tubular member 202 may be vertically tilted, e.g., in a clockwise direction from the orientation illustrated in FIG. 16, to a use position wherein elongated tubular member 202 is disposed at an oblique angle relative the longitudinal axis of frame 1402. From there, elongated tubular member may be advanced and retracted proximally and distally, respectively; rotated about its axis; and/or further vertically tiled to facilitate use thereof. Upon the vertical tilting and further vertical tilting of elongated tubular member 202, a more-proximal portion of elongated tubular member 202 enters proximal section 1424 of longitudinal portion 1420 from the open lower side thereof (see FIG. 14B) while a more-distal portion of elongated tubular member 202 enters distal section 1426 of longitudinal portion 1420 from the open upper side thereof (see FIG. 14C). Sterile barrier 1460 is flexed upwardly and downwardly to permit this tilting and insertion of the more-proximal and more-distal portions, respectively, of elongated tubular member 202 into frame 1402. Elongated tubular member 202 may be tilted to a substantially coaxial orientation relative to the longitudinal axis defined by longitudinal portion 1420 of frame 1402 without compromising sterile barrier 1460 but is inhibited from tilting substantially therebeyond due to the presence of first and second backspans 1407, 1408, respectively.

Figure 17A:
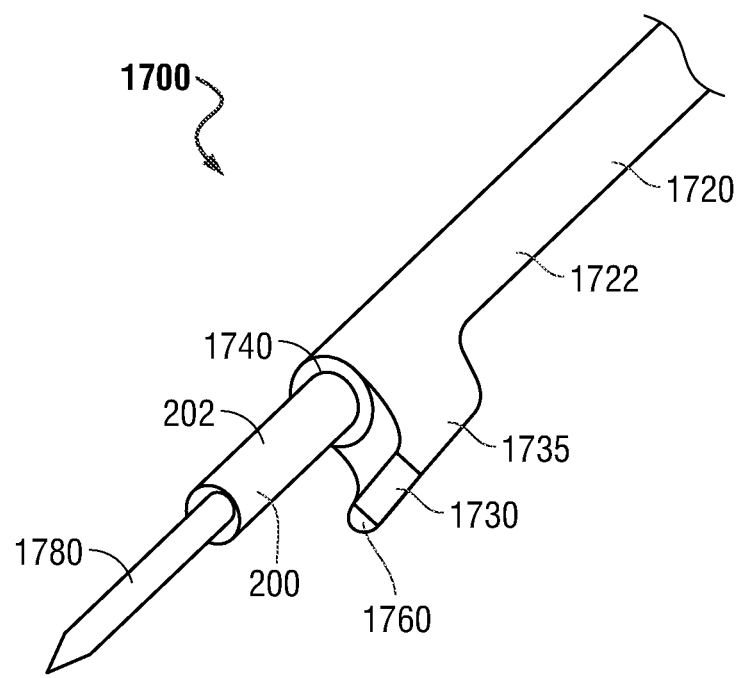
FIG. 17A is a perspective view of another ultrasound device including a hysteroscope and working instrument inserted therethrough.
Figure 17B:
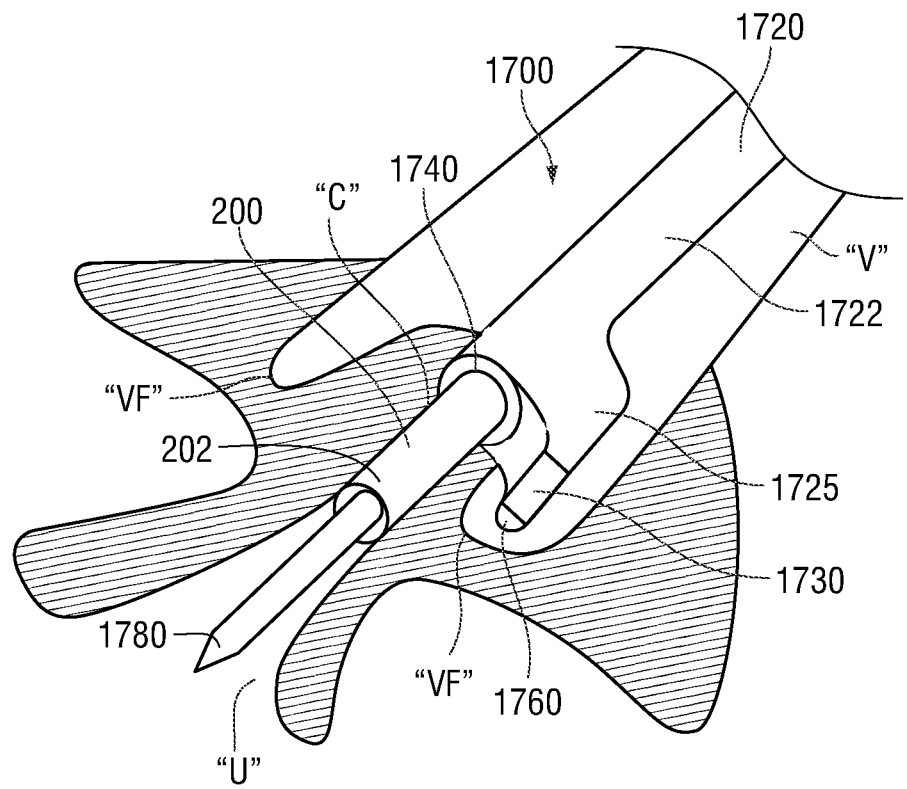
FIG. 17B is a perspective view of the ultrasound device of FIG. 17A positioned adjacent the cervix with the hysteroscope and working instrument extending through the cervix and into the uterus.

Referring to FIGS. 17A and 17B, still yet another ultrasound device provided in accordance with the present disclosure is shown generally identified by reference numeral 1700. Ultrasound device 1700 is similar to and may include any of the features of ultrasound device 300 (FIGS. 1 and 2), detailed above. Thus, only differences between ultrasound device 1400 and ultrasound device 300 (FIGS. 1 and 2) are described in detail below while similarities are summarily described or omitted entirely.

Ultrasound device 1700 includes a proximal body (not shown), a shaft 1720 extending distally from the proximal body, and an ultrasound sensor assembly 1730 disposed at a distal end portion of shaft 1720. In some configurations, the proximal body is omitted. Ultrasound device 1700 further includes a longitudinal lumen 1740 defined through shaft 1720 that is configured to permit passage of at least a portion of an endoscope device e.g., elongated tubular member 202 of hysteroscope 200. A working instrument such as, for example, an ablation probe 1780, may be passed through elongated tubular member 202 of hysteroscope 200.

A body portion 1722 of shaft 1720 defines a generally cylindrical configuration coaxially disposed about lumen 1740. Shaft 1720 further includes a distal leg 1725 extending distally from a distal end portion thereof. Distal leg 1725 defines a foot 1760 at the free end portion thereof. Ultrasound sensor assembly 1730 is disposed within foot 1760 and, in aspects, may be angled such that the field of view produced by ultrasound sensor assembly 1730 is centered a pre-determined longitudinal distance from the distal end of shaft 1720 along the longitudinal axis thereof, e.g., such that the distal end of elongated tubular member 202 and/or the distal end of ablation probe 1780 are maintained within the field of view during manipulation within the uterus "U" and/or surrounding tissue(s). Distal leg 1725 and foot 1760 protrude distally from the distal end of body 1722 of shaft 1720 at a position radially offset relative to a longitudinal axis defined by body portion 1722 of shaft 1720 sufficiently such that an annular volume is defined between elongated tubular member 202 (when extending distally from through lumen 1740) and foot 1760 regardless of the orientation of ultrasound device 1700 relative to elongated tubular member 202. Distal leg 1725 and foot 1760 are configured such that the annular volume defines a substantially (e.g., within 10%) constant width dimension along a least a portion of a longitudinal distance from the distal end of body portion 1722 of shaft 1720 to the distal end of foot 1760. More specifically, the annular volume may define a substantially (e.g., within 10%) constant width along at least 50% of the longitudinal distance, at least 70% of the longitudinal distance, or at least 90% of the longitudinal distance.

As a result of the above-detailed configuration wherein distal leg 1725 and foot 1760 protrude distally from the distal end of body 1722 of shaft 1720 at a radially offset position, as ultrasound device 1700 is rotated about elongated tubular member 202, foot 1760 is orbited annularly about elongated tubular member 202, maintaining the annular volume therebetween. In use, as shown in FIG. 17B, ultrasound device 1700 can be positioned with the distal end of body portion 1722 of shaft 1720 abutting the cervix "C" (to enable insertion of elongated tubular member 202 and ablation probe 1780 through the cervix "C" and into the uterus "U") while foot 1760 (containing ultrasound sensor assembly 1730) is maintained in contact with a vaginal fornix "VF." More specifically, the annular volume defined between elongated tubular member 202 and leg 1725 and foot 1760 receives the portion of the cervix "C" that protrudes into the vaginal canal "V," thus enabling foot 1760 to extend into contact with a vaginal fornix "VF." Maintaining tissue contact ensures proper transmission contact between ultrasound sensor assembly 1730 and tissue, thus facilitating ultrasound imaging. With respect to ultrasound device 1700 or any other ultrasound device detailed herein, ultrasound gel may be utilized to facilitating maintaining proper transmission contact.

Continuing with reference to FIG. 17B, ultrasound device 1700 may be rotated about elongated tubular member 202 to position foot 1760 in contact with different vaginal fornices "VF." The various different positions of ultrasound device 1700 provide various different fields of view and/or viewing perspectives to facilitate ultrasound imaging, e.g., to identify the target tissue to be ablated using ablation probe 1780 or for performing any other surgical task(s). For example, ultrasound device 1700 may be rotated to achieve a desired field or view and/or viewing perspective and them maintained in position while performing the ablation or other surgical task. Alternatively, ultrasound device 1700 may be rotated to various different rotational positions to enable the ultrasound console (not shown) to generate and display a 3D image of the patient's anatomy. This may be accomplished in a robotic implementation (see FIG. 20) whereby the rotation of ultrasound device 1700 can be readily controlled, although manual implementations are also contemplated. The 3D image may be generated for later use or may be continually updated during the procedure.

Figure 18:
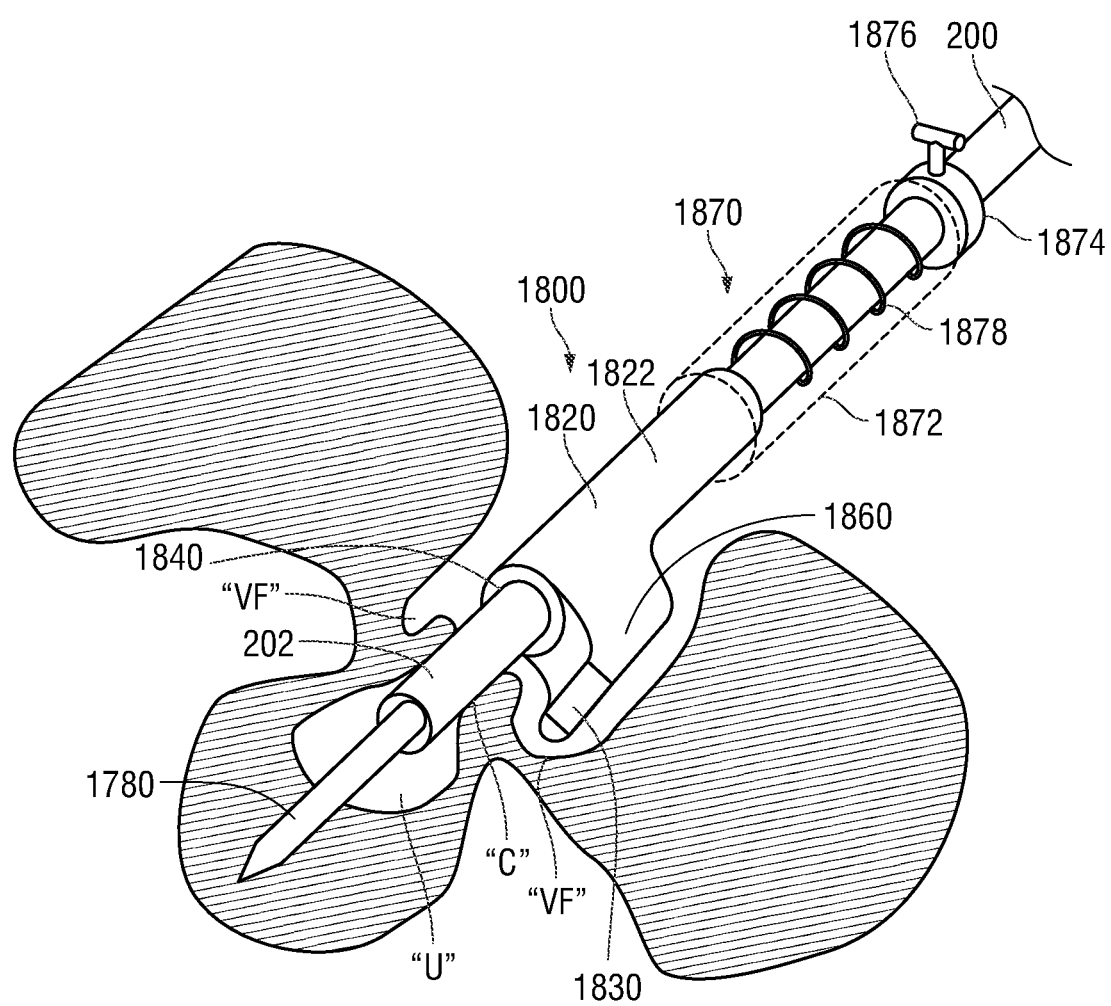
FIG. 18 is a perspective view of another ultrasound device positioned adjacent the cervix with a hysteroscope and working instrument extending through the cervix and into the uterus.

With reference to FIG. 18, another ultrasound device 1800 in accordance with the present disclosure includes a shaft 1820, an ultrasound sensor assembly 1830, and a bias assembly 1870. Shaft 1820 and ultrasound sensor assembly 1830 may be similar to and include any of the features of shaft 1720 and ultrasound sensors assembly 1730 of ultrasound device 1700 (FIGS. 17A and 17B), the features of any of the other configurations detailed herein, or any other suitable configuration. Accordingly, shaft 1820 and ultrasound sensor assembly 1830 are not described in detail hereinbelow.

Bias assembly 1870 includes an outer sleeve 1872 configured to telescopically receive a proximal end portion of body 1822 of shaft 1820, a lock collar 1874 disposed at a proximal end of outer sleeve 1872, a set screw 1876 (or other suitable locking element) operably engaged with lock collar 1874, and a biasing member 1878 (e.g., a coil spring), disposed within outer sleeve 1872 and extending between lock collar 1874 and a proximal end face of body 1822 of shaft 1820 to bias body 1822 of shaft 1820 distally relative to lock collar 1874. Body 1822 of shaft 1820 and/or outer sleeve 1872 may include stop features (not explicitly shown) configured to inhibit full removal and decoupling of body 1822 of shaft 1820 from outer sleeve 1872. Further, outer sleeve 1872, the proximal end face of body 1822, and/or lock collar 1874 may include retention features (not explicitly shown) to fix the ends of biasing member 1878 or otherwise retain biasing member 1878 relative to outer sleeve 1872, the proximal end face of body 1822, and/or lock collar 1874.

Shaft 1820 of ultrasound device 1800 defines a longitudinal lumen 1840 therethrough that is configured to slidably receive at least a portion of an endoscope device e.g., elongated tubular member 202 of hysteroscope 200. Bias assembly 1870 likewise defines an internal passage aligned with lumen 1840 to receive elongated tubular member 202 therethrough. With elongated tubular member 202 received through bias assembly 1870, set screw 1876 may be tightened through lock collar 1874 and against elongated tubular member 202 to fix lock collar 1874 about elongated tubular member 202. Shaft 1820 and bias assembly 1870 may be configured such that lock collar 1874 remains external of the patient while shaft 1820 extends transvaginally into a position adjacent the cervix "C," thus enabling selective locking and unlocking of bias assembly 1870 with elongated tubular member 202 during use.

In use, ultrasound device 1800 is positioned with the distal end of body portion 1822 of shaft 1820 abutting the cervix "C" and with elongated tubular member 202 (and ablation probe 1780 therein) extending through the cervix "C" and into the uterus "U." After insertion, or prior thereto, set screw 1876 may be tightened through lock collar 1874 and against elongated tubular member 202 to fix lock collar 1874 about elongated tubular member 202. In this locked condition of lock collar 1874, ultrasound device 1800 is operably coupled with elongated tubular member 202 of hysteroscope 200 such that ultrasound device 1800 and elongated tubular member 202 may be manipulated as a unit, e.g., via a single hand of a user (manipulating the handle of hysteroscope 200, for example). Further, in this locked condition, biasing member 1878 biases body 1822 of shaft 1820 distally relative to elongated tubular member 202 such that foot 1860 of shaft 1820 is biased distally into contact with a vaginal fornix "VF," ensuring proper transmission contact between ultrasound sensor assembly 1830 and tissue. More specifically, further distal advancement of elongated tubular member 202 into the uterus "U," e.g., to facilitate performing a surgical task therein, is permitted without applying excess force to the cervix "C" or vaginal fornices "VF" due to the compression of biasing member 1878 (against its bias) which allows sliding of outer sleeve 1872 distally about body 1822 of shaft 1820, thus enabling distal movement of elongated tubular member 202 relative to shaft 1820. In addition, proper transmission contact between ultrasound sensor assembly 1830 and tissue is maintained despite proximal retraction of elongated tubular member 202 from the uterus "U." That is, as elongated tubular member 202 is retracted proximally, biasing member 1878 is resiliently elongated (under its bias) such that shaft 1820 is maintained in position in contact with tissue despite the relative proximal translation of elongated tubular member 202 relative to shaft 1820. The length of outer sleeve 1872 and the length of biasing member 1878 (in at-rest, fully compressed, and/or fully elongated positions) determine the amount of distal advancement and proximal retraction permitted and may be selected to enable sufficient distal advancement and proximal retraction as required to manipulate elongated tubular member 202 with the uterus "U" during use.

Figure 19:
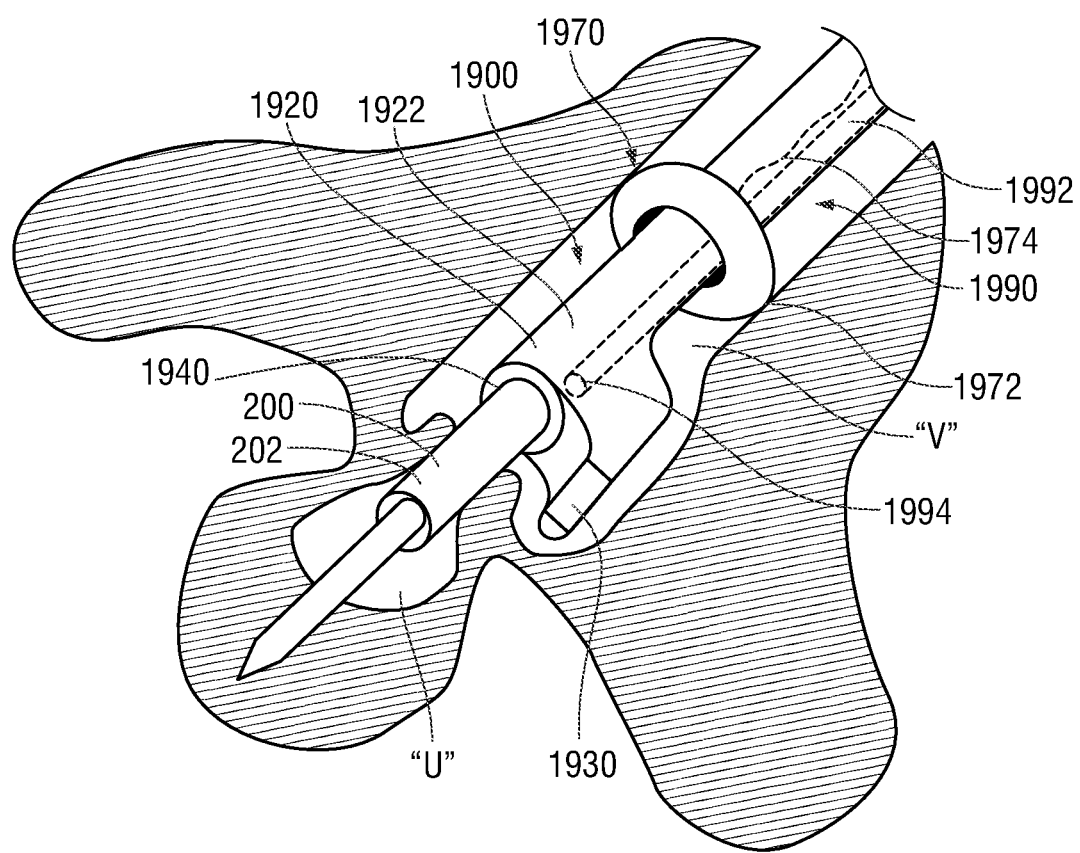
FIG. 19 is a perspective view of another ultrasound device positioned adjacent the cervix with a hysteroscope and working instrument extending through the cervix and into the uterus.

With reference to FIG. 19, yet another ultrasound device 1900 in accordance with the present disclosure includes a shaft 1920, an ultrasound sensor assembly 1930, an occlusion assembly 1970, and a fluid supply assembly 1990. Ultrasound device 1900 may be similar to and include any of the features of ultrasound device 1700 (FIGS. 17A and 17B), the features of any of the other ultrasound devices detailed herein, or any other suitable configuration. Accordingly, only the additional features of ultrasound device 1900 are described in detail hereinbelow.

Occlusion assembly 1970 of ultrasound device 1900 includes an inflatable balloon 1972 disposed about body 1922 of shaft 1920, and an inflation fluid line 1974 fluidly coupled to inflatable balloon 1972 and extending proximally through (or along) shaft 1920 to connect to an inflation fluid source, e.g., an inflation fluid pump connected to an inflation fluid reservoir (not shown), to enable the selective inflation and deflation of inflatable balloon 1972. Inflatable balloon 1972 defines a donut-shaped configuration such that, with ultrasound device 1900 positioned within the vaginal canal "V," inflatable balloon 1972 may be inflated, e.g., via pumping inflation fluid through fluid line 1974 into inflatable balloon 1972, to thereby expand inflatable balloon 1972 to sealingly engage the internal walls of the vaginal canal "V" and occlude the vaginal canal "V."

Fluid supply assembly 1990 includes an infusion fluid conduit 1992 extending through (or along) shaft 1920 to one or more distal openings 1994 positioned distally of inflatable balloon 1972. Infusion fluid conduit 1992 is configured to extend proximally to connect to an infusion fluid source, e.g., an infusion fluid pump connected to an infusion fluid reservoir (not shown), to enable the selective infusion or withdrawal of infusion fluid to/from the occluded portion of the vaginal canal "V" via distal opening(s) 1994 of infusion fluid conduit 1992. As an alternative to fluid supply assembly 1990 incorporated into ultrasound device 1900, a separate fluid supply assembly may be utilized, e.g., inserted through lumen 1940 of shaft 1920 of ultrasound device 1900 or through elongated tubular member 202 of hysteroscope 200. The pumping of infusion fluid, e.g., saline or other suitable fluid, into the occluded portion of the vaginal canal "V" provides a transmission medium for the passage of ultrasound from ultrasound sensor assembly 1930 to tissue without requiring direct contact between ultrasound sensor assembly 1930 and tissue, thus increasing the positionability of ultrasound device 1900 to enable ultrasound visualization of, e.g., the uterus "U." Fluid infusion in this manner may additionally or alternatively be utilized for other purposes, or may be omitted, whereby inflatable balloon 1972 is utilized to provide stabilization and maintain the position of ultrasound device 1900 within the patient.

Turning to FIG. 20, a robotic surgical system 1000 configured for use in accordance with the present disclosure is shown. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 506, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and a mounted device which may be, for example, a surgical tool "ST." The surgical tools "ST" may include, for example, any of the ultrasound devices of the present disclosure, a hysteroscope (or endoscope), a working instrument, etc., thus providing any of the above-detailed functionality on a robotic surgical system 1000.

Robot arms 1002, 1003 may be driven by electric drives, e.g., motors, connected to control device 1004. The motors, for example, may be rotational drive motors configured to provide rotational inputs to accomplish a desired task or tasks. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Control device 1004, more specifically, may control one or more of the motors based on rotation, e.g., controlling to rotational position using a rotational position encoder (or Hall effect sensors or other suitable rotational position detectors) associated with the motor to determine a degree of rotation output from the motor and, thus, the degree of rotational input provided. Alternatively or additionally, control device 1004 may control one or more of the motors based on torque, current, or in any other suitable manner.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A surgical system, comprising:
  an ultrasound device, including:
    a frame defined by first and second rails spaced apart relative to one another, the frame including a longitudinal section defining a longitudinal axis, the longitudinal section having a distal end portion; and
    an ultrasound sensor assembly configured to enable ultrasound imaging of a two-dimensional field of view in a viewing direction, the ultrasound sensor assembly being attached to the distal end portion of the longitudinal section of the frame, wherein the ultrasound sensor assembly is disposed in fixed orientation relative to the longitudinal axis with the viewing direction of the two-dimensional field of view disposed at an oblique angle relative to the longitudinal axis and with the longitudinal axis extending coplanarly through the two dimensional field of view, wherein the distal end portion of the longitudinal section of the frame is configured for insertion through a vagina of a patient to position the ultrasound sensor assembly adjacent to or in abutment with a cervix of the patient, wherein the longitudinal section of the frame and the ultrasound sensor assembly cooperate to define a hollow interior extending along the longitudinal axis, the hollow interior closed at a distal end of the hollow interior, closed on opposing sides of the hollow interior by the first and second rails, and open along the top and the bottom of the hollow interior along the longitudinal axis; and a surgical instrument configured for insertion between the first and second rails at an oblique angle relative to the longitudinal axis such that the surgical instrument extends into the hollow interior through one of the top or the bottom of the hollow interior and out of the hollow interior from another of the top or the bottom of the hollow interior, the surgical instrument configured for insertion, from between the first and second rails through the vagina of the patient, through the cervix of the patient, and into a uterus of the patient, wherein the first and second rails constrain transverse movement of the surgical instrument to maintain the surgical instrument in coplanar relation relative to the two-dimensional field of view of the ultrasound sensor assembly.

2. The surgical system according to claim 1, wherein the frame of the ultrasound device further includes an upright section disposed at an angle relative to the longitudinal section and a bend interconnecting the upright section and a proximal end portion of the longitudinal section.

3. The surgical system according to claim 2, wherein the surgical instrument is insertable between the first and second rails of the frame at the bend of the frame or the upright section of the frame in parallel or coaxial orientation relative to the longitudinal axis of the longitudinal section of the frame.

4. The surgical system according to claim 1, wherein first and second rails constrain transverse movement of the surgical instrument while permitting axial translation, axial rotation, and vertical tilting of the surgical instrument when the surgical instrument is inserted between the first and second rails.

5. The surgical system, according to claim 1, wherein the ultrasound device further includes at least one spacer disposed between the first and second rails, the at least one spacer securing the first and second rails to one another and maintaining spacing between the first and second rails.

6. The surgical system according to claim 1, wherein the first and second rails of the frame of the ultrasound device are parallel plates.

7. The surgical system according to claim 1, further comprising a sterile barrier disposed about the ultrasound sensor assembly and at least a portion of the longitudinal section of the frame.

8. The surgical system according to claim 7, wherein the surgical instrument, when inserted between the first and second rails, remains external of the sterile barrier.

9. The surgical system according to claim 1, wherein the ultrasound device further includes a lock disposed between the first and second rails, the lock configured to selectively retain the surgical instrument between the first and second rails in fixed position and orientation relative to the first and second rails.

10. The surgical system according to claim 1, wherein the surgical device is a hysteroscope configured to receive a working instrument.

* * * * *